United States Patent
Bahatt et al.

(10) Patent No.: US 7,108,775 B2
(45) Date of Patent: Sep. 19, 2006

(54) APPARATUS AND METHOD FOR CONFINING ELUTED SAMPLES IN ELECTROPHORESIS SYSTEMS

(75) Inventors: Dar Bahatt, Foster City, CA (US); Reid Kowallis, Burlingame, CA (US)

(73) Assignee: Applera Corporation, Foster City, CA (US)

( * ) Notice: Subject to any disclaimer, the term of this patent is extended or adjusted under 35 U.S.C. 154(b) by 574 days.

(21) Appl. No.: 10/291,088

(22) Filed: Nov. 8, 2002

(65) Prior Publication Data

US 2004/0089546 A1     May 13, 2004

(51) Int. Cl.
*G01N 27/447* (2006.01)

(52) U.S. Cl. .................. 204/601; 204/451; 204/452; 204/603

(58) Field of Classification Search ........ 204/450–455, 204/601–605
See application file for complete search history.

(56) References Cited

U.S. PATENT DOCUMENTS

| | | | |
|---|---|---|---|
| 4,675,095 A | | 6/1987 | Kambara et al. |
| 4,908,112 A | * | 3/1990 | Pace ................. 210/198.2 |
| 5,126,021 A | | 6/1992 | Grossman |
| 5,184,192 A | | 2/1993 | Gilby et al. |
| 5,268,080 A | | 12/1993 | Kambara et al. |
| 5,277,780 A | | 1/1994 | Kambara |
| 5,374,527 A | | 12/1994 | Grossman |
| 5,412,750 A | | 5/1995 | Nath |
| 5,414,508 A | | 5/1995 | Takahashi et al. |
| 5,439,578 A | | 8/1995 | Dovichi et al. |
| 5,444,807 A | | 8/1995 | Liu |

(Continued)

FOREIGN PATENT DOCUMENTS

EP       0321736 B1    6/1989

(Continued)

OTHER PUBLICATIONS

Kameoka J et al., "An Electrospray Ionization Source for Integration With Microfluidics," vol. 22 No. 74, Nov. 15, 2002, pp. 5897-5901.

(Continued)

*Primary Examiner*—Alan Diamond
*Assistant Examiner*—Jeffrey Barton

(57) ABSTRACT

The present teachings provide a microfluidic apparatus comprising a body defining at least one channel that extends through said body, the channel including an inlet and an outlet; and an electrode positioned in proximity to the body and configured to provide an electrical field near the outlet of the channel to at least partially confine an eluted sample component passing from the channel. The present teachings also provide an electrophoresis system, comprising a microfluidic chip defining a plurality of channels passing therethrough, each of the channels having an inlet and an outlet; a first electrode in electrical communication with the inlet of each of the channels; a second electrode in electrical communication with the outlet of each of the channels; and a third electrode in electrical communication with the outlet of each of the channels, wherein the third electrode is positioned to provide an electrical field to at least partially confine an eluted sample component passing from any of the channels. The present teachings also provide a method for confining a sample component eluting from a channel of a microfluidic chip, comprising generating an electrical field in proximity to an outlet of a channel in a microfluidic chip to at least partially confine an eluted sample component passing from the channel, thereby reducing distortion of the eluted sample component and mixing with an adjacent eluted sample component.

8 Claims, 17 Drawing Sheets

U.S. PATENT DOCUMENTS

| | | | |
|---|---|---|---|
| 5,516,409 A | 5/1996 | Kambara | |
| 5,529,679 A | 6/1996 | Takahashi et al. | |
| 5,546,493 A | 8/1996 | Noguchi et al. | |
| 5,567,292 A | 10/1996 | Madabhushi et al. | |
| 5,583,826 A | 12/1996 | Soubaras | |
| 5,584,982 A | 12/1996 | Dovichi et al. | |
| 5,608,517 A | 3/1997 | Munk | |
| 5,667,656 A | 9/1997 | Kambara | |
| 5,803,575 A | 9/1998 | Ansems et al. | |
| 5,815,258 A | 9/1998 | Nakanishi | |
| 5,833,826 A | 11/1998 | Nordman | |
| 5,833,827 A | 11/1998 | Anazawa et al. | |
| 5,857,052 A | 1/1999 | Nath | |
| 5,858,187 A | 1/1999 | Ramsey et al. | |
| 5,858,195 A | 1/1999 | Ramsey et al. | |
| 5,900,934 A | 5/1999 | Gilby et al. | |
| 5,991,081 A | 11/1999 | Haaland et al. | |
| 6,017,765 A | 1/2000 | Yamada et al. | |
| 6,020,207 A | 2/2000 | Liu | |
| 6,062,261 A | 5/2000 | Jacobson et al. | |
| 6,068,751 A | 5/2000 | Neukermans | |
| 6,103,199 A * | 8/2000 | Bjornson et al. | 422/100 |
| 6,143,152 A | 11/2000 | Simpson et al. | |
| 6,162,341 A | 12/2000 | Nordman et al. | |
| 6,188,813 B1 | 2/2001 | Dourdeville et al. | |
| 6,284,113 B1 | 9/2001 | Bjornson et al. | |
| 6,306,273 B1 | 10/2001 | Wainright et al. | |
| 6,306,590 B1 | 10/2001 | Mehta et al. | |
| 6,306,659 B1 | 10/2001 | Parce et al. | |
| 6,316,201 B1 | 11/2001 | Nikiforov | |
| 6,485,626 B1 * | 11/2002 | Bottani et al. | 204/603 |
| 2002/0162745 A1 | 11/2002 | Nordman | |

FOREIGN PATENT DOCUMENTS

| | | |
|---|---|---|
| EP | 0 723 149 A | 7/1996 |
| WO | WO 93/17325 | 1/1993 |
| WO | WO 99/46589 A1 | 9/1999 |
| WO | WO 03/013703 A1 | 2/2003 |

OTHER PUBLICATIONS

Smith A D et al., "Control of Electrochemical Reactions At The Capillary Electrophoresis Outlet/Electrospray Emitter Electrode Under CE/ESI-MS Through The Application of Redox Buffers," vol. 73, No. 2, Jan. 15, 2001 pp. 240-246.

International Search Report from PCT/US03/35962 mailed Oct. 11, 2004.

U.S. Appl. No. 09/812,750, filed Sep. 19, 2002, Bahatt et al.

U.S. Appl. No. 09/938,947, filed Apr. 24, 2003, Waidenberg et al.

Alentiev et al., 1996 "High transport parameters and free volume of perfluorodioxole copolymers" *Journal of Membrane Science 126* (1997) 123-132.

Douthart et al., 1996, "Ribbon Channel Plate Rotating Drum DNA Sequencing Device" *Electrophoresis 17*, 49-54.

Gooijer et al., 1998 "Detector cell based on plastic liquid-core waveguides suitable for aqueous solutions: one-to-two decades improved detection limits in conventional-size column liquid chromatography with absorption detection" *Journal of Chromatography A*, 824 (1998) 1-5.

Haab et al., 1999, "Single-Molecule Detection of DNA Separations in Microfabricated Capillary Electrophoresis Chips Employing Focused Molecular Systems," Anal. Chem. 1999, 71, 5137-5145.

McCormick et al., 1997, "Microchannel Electrophoretic Seprations of DNA in Injection -Molded Plastic Substrates" *Anal. Chem.* 1997, 69 2626-2630.

Pinnau et al., 1995 "Gas and vapor transport properties of amorphous perfluorinated copolymer membranes based on 2,2-bistrifluoromethyl-4,5-difluoro-1,3-dixole/tetrafluornoethynylene" *Journal of Membrane Science 109* (1996) 125-133.

Polson et al., 1999, "Electrophoretic Focusing Preconcentration Technique Using a Continuous Buffer System for Capillary Electrophoresis," *J. Microcolumn Separations*, 21(2) 98-106.

Waterbury et al., 1997, "Long pathlength absorbance spectroscopy: trace analysis of Fe(II) using a 4.5 m liquid core waveguide" *Analytica Chimica Acta 357* (1997) 99-102.

* cited by examiner

APPARATUS AND METHOD FOR CONFINING ELUTED SAMPLES IN ELECTROPHORESIS SYSTEMS

FIELD

The present teachings relate generally to devices and methods for electrophoresis systems. More particularly, the present teachings are directed to an apparatus and method for at least partially confining eluted samples passing from channels in an electrophoresis microfluidic chip.

BACKGROUND

In biotechnology, separation and analysis of biological samples is critically important. Moreover, it is desirable to conduct multiple separations and analyses of the separated components simultaneously to increase the speed and efficiency at which chemical samples are evaluated. For example, separation technologies such as electrophoresis are used in DNA sequencing, protein molecular weight determination, genetic mapping, and other types of processes used to gather large amounts of analytical information about particular chemical samples.

One method used to separate chemical samples into their component parts is electrophoresis. Electrophoresis is the migration of charged colloidal particles or molecules through a solution under the influence of an applied electric field usually provided by immersed electrodes, where the colloidal particles are a suspension of finely divided particles in a continuous media. Historically, a polymer gel containing the finely divided particles is placed between two glass plates and an electric field applied to both ends of the plates. This method, however, offers a low level of automation and long analysis times.

More recently, the capillary electrophoresis method was developed, which has the added advantages of speed, versatility and low running costs. Operation of a capillary electrophoresis system involves application of a high voltage (typically 5–15 kV) across a narrow bore capillary (typically 25–100 μm). The capillary is filled with electrolyte solution that conducts current through the inside of the capillary. The ends of the capillary are placed in reservoirs filled with the electrolyte. Electrodes made of an inert material such as platinum are also inserted into the electrolyte reservoirs to complete the electrical circuit. A small volume of sample is injected into one end of the capillary. Application of a voltage across the capillary causes movement of the sample ions towards a corresponding electrode at the opposite end of the capillary. Depending upon various factors, the different components in the sample will travel through the capillary at different rates. Therefore, the sample will be separated into its various components or at least into those components that travel through the capillary at the same rate. A detector, such as a emission detector, is positioned at the opposite end of the capillary to detect the presence of the various sample components as they travel through the capillary and past the detector. The sample may be labeled with a fluorescent marker so that when the sample components pass through a beam of light at the detector, the fluorescent marker fluoresces, and the fluorescence is detected as an electric signal. The intensity of the electric signal depends on the amount of fluorescent marker present in the detection zone. The plot of detector response with time is then generated which is termed an electropherogram.

In traditional capillary electrophoresis systems, analysis or detection of the separated components is performed while the sample is still located within the capillary and may be accomplished using photometric techniques such as absorbance and fluorescence. Absorbance and fluorescence is where excitation light is directed toward the capillary tube, and light emitted from the sample (e.g., fluorescence) is measured by a detector, thereby providing information about the separated components. Therefore, in these systems, excitation light directed at the sample, as well as light emitted from the sample, must be transmitted through the capillary's walls. A drawback of this approach is that the tubular shape of the fused silica capillaries causes significant scattering of light. The problem associated with light scattering is exacerbated by the fact that silica itself gives off a background level of fluorescence and further by having multiple capillaries disposed side-by-side, as scattered excitation light from one capillary interferes with the detection of samples in neighboring capillaries.

A preferred variation of the capillary electrophoresis system described above replaces the capillary tubes with a number of parallel channels formed in a substrate such as a plate or chip, where the channels are in fluid communication with a pair of electrodes. This type of system is known, for example, as a microfluidic chip or micro-channel array. Such microfluidic chips are advantageous for high-throughput applications where a large number of samples are to be separated or otherwise manipulated at one time. However, similar to the traditional capillary electrophoresis system described above, on-chip detection or detecting or analyzing separated components within a chip, is problematic as excitation light is scattered or otherwise disrupted by the substrate material surrounding each of the micro-channels in the chip, since a substrate material such as plastic has a higher background fluorescence compared to glass.

One approach to solving the problem of on-chip detection, which has also been employed in capillary systems, is to detect separated or eluted sample components in a detection cell positioned adjacent to, but physically separate from, the chip or capillary system. This may be referred to as "off-chip" detection. The detection cell houses a polymer matrix through which the eluted sample components pass; however, there are no other structural components within the detection cell. The eluted sample components in this case simply traverse or pass through the polymer matrix from the inlet end of the detection cell to the outlet end. Since there are no other physical structures within the detection cell, excitation light that is directed into the detection cell only passes through the outer detection cell wall and through the polymer matrix rather than through multiple channel walls or capillary tube walls. This results in less scattering of the excitation light. The location within the detection cell where such excitation light is passed may be referred to as a "detection zone."

The composition and configuration of the detection cell are selected to provide superior optical characteristics, e.g., a flat quartz chamber or low refractive index material. U.S. patent application Ser. No. 09/812,750, filed Mar. 19, 2001 and entitled "Detection Cell For Guiding Excitation Light Therein and Method For Using Same," incorporated herein in its entirety by reference, is directed to such a detection cell that is made of a material having a low index of refraction lower than the polymer matrix to further reduce scattering by confining the excitation light between the walls of the detection cell having the lower index of refraction.

Maintaining the integrity of the eluted sample components in the polymer matrix of the detection cell, however, is important. In other words, as the eluted samples pass through the polymer matrix of a detection cell, the eluted sample components tend to distort or disperse in both vertical and horizontal directions, thereby reducing detection signal intensity and interfering with adjacent eluted sample components. Therefore, it is important to confine the eluted sample components to a "path" in the polymer matrix of the detection cell so that the eluted sample components will pass through the detection cell without significant dispersion.

In some capillary systems, such eluted sample components exiting the capillary are transported by a "sheath flow" of liquid through the detection cell to a detection zone within the detection cell where detection or analysis of the sample band takes place. A drawback of sheath flow systems is that in order to avoid distortion of a sample component, precise control of the flow rate of the sheath flow liquid is required. Another drawback of sheath flow systems is that the pressure used to drive the flow of the sheath flow liquid can cause back flow of the separation media in the channels, thereby impacting resolution. Further, the liquid flow that creates the "sheath" imparts a velocity profile to the eluted sample component, which, in turn, affects the index of refraction and the resolution.

In other off-chip detection systems, an eluted sample component (including an eluted sample component that is a discrete peak or band and an eluted sample component that elutes as a continuous stream) is transported from the outlet of the channels to a detection zone located in a detection cell by electrophoresis under the influence of the same voltage difference used to conduct the electrophoretic separation. Examples of capillary electrophoresis apparatus employing such detection systems are found, for example, in U.S. Pat. Nos. 5,529,679 by Takahashi et al and 5,583,826 by Nordman, both of which are incorporated herein in their entirety by reference. However, because of the larger cross-sectional area of the detection cell as compared to the lumen of the channels, the electric field diverges at each channel outlet causing a distortion of an eluted sample component. Such distortion results in severe loss of spatial resolution between subsequent sample components eluting from a single channel and between sample components eluting from adjacent channels. This loss of spatial resolution tends to reduce the detectability of these sample components and may result in actual mixing of the sample components or optical cross-talk between such sample zones.

FIG. 1 is a schematic top view of a portion of a microfluidic electrophoresis chip and illustrates the problem of distortion of sample components eluted from a microfluidic chip. FIG. 1 illustrates a microfluidic chip 100 having channels 104 through which charged sample components or bands 102 pass under a voltage applied between two electrodes 106, 108. As shown, discrete sample bands 102 are present within the channels 104 of the chip 100. Upon exiting the channels 104, however, the sample bands 102 are distorted while moving along their electrophoretic flow paths 110, as the sample bands 102 tend to follow the exemplary, divergent flow lines 112 (shown for one channel only).

Thus, there remains a need for an improved system and method for confining or otherwise reducing distortion of eluted sample components (including both eluted sample components that elute as discrete peaks or bands and those that elute as a continuous stream) passing from channels in a microfluidic chip or similar device.

SUMMARY

The present teachings provide a microfluidic device capable of confining, or at least partially confining, discrete sample components and/or streams of sample components eluting from channels in the device, for example, during electrophoretic separation of a sample of charged particles. In particular, the apparatus of the present teachings provides an electrical pinching field that confines, in up to three dimensions, streams or bands of charged particles eluting from channels in a microfluidic chip or similar device. The microfluidic chips of the present teachings can be used in conjunction with laser-induced fluorescence detection techniques conducted in a detection cell after samples exit the channels of a chip.

In one embodiment, the present teachings provide a microfluidic apparatus comprising a body defining at least one channel that extends through said body, the channel including an inlet and an outlet; and an electrode positioned in proximity to the body and configured to provide an electrical field near the outlet of the channel to at least partially confine an eluted sample component passing from the channel.

In another embodiment, the present teachings also provide an electrophoresis system, comprising a microfluidic chip defining a plurality of channels passing therethrough, each of the channels having an inlet and an outlet; a first electrode in electrical communication with the inlet of each of the channels; a second electrode in electrical communication with the outlet of each of the channels; and a third electrode in electrical communication with the outlet of each of the channels, wherein the third electrode is positioned to provide an electrical field to at least partially confine an eluted sample component passing from any of the channels.

In another embodiment, the present teachings also provide a method for confining a sample component eluting from a channel of a microfluidic chip, comprising generating an electrical field in proximity to an outlet of a channel in a microfluidic chip to at least partially confine an eluted sample component passing from the channel, thereby reducing distortion of the eluted sample component and mixing with an adjacent eluted sample component.

The present teachings provide a novel apparatus and method for confining an eluted sample component exiting from a channel of a microfluidic chip. The apparatus and method of the present teachings thereby reduce distortion of an eluted sample component in the detection cell, which provides for better sample component detection and avoidance of mixing with adjacent sample components that have eluted from adjacent channels of the microfluidic device.

DESCRIPTION OF VARIOUS EMBODIMENTS

Figure 1:
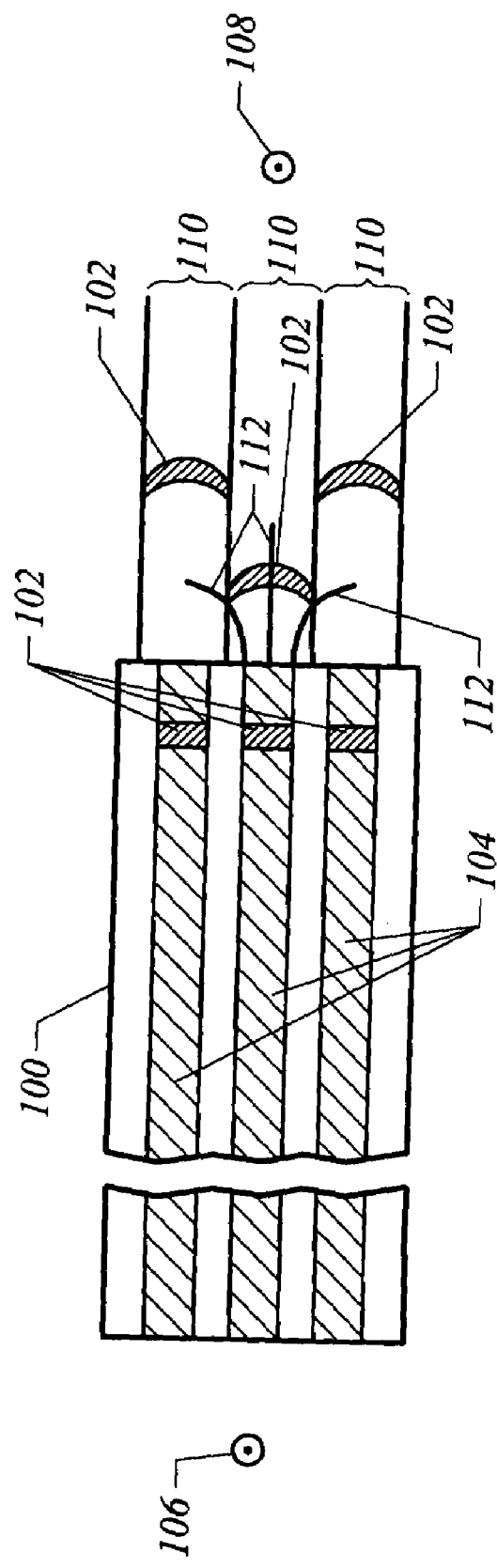
FIG. 1 is a schematic top view of a portion of a microfluidic electrophoresis chip.

The structure and function of the various embodiments of the microfluidic apparatus and methods of the present teachings can best be understood by reference to the drawings. Where the same reference designations appear in multiple locations in the drawings, the numerals refer to the same or corresponding structure in those locations. While the present teachings will be described in conjunction with the various embodiments, it will be understood that they are not intended to limit the present teachings to those particular embodiments. On the contrary, the present teachings are intended to cover alternatives, modifications, and equivalents, which may be included within the present teachings as defined by the appended claims.

The term "microfluidic chip," as use herein, includes not only a plastic or silicon or glass chip but also any substrate, such as a slide, wafer, disc, etc. capable of having a number of small channels or groves formed therein for passing charged particles.

The term "channel" as used herein refers to a passage through a substrate. The geometry of a channel may vary widely and includes tubular passages with circular, rectangular, square, D-shaped, or other polygonal cross-sections. Channels may also be grooves or troughs formed on one side of a substrate, and they may be fabricated using a wide range of technologies. Channels may form curved or angular paths through the substrate, and they may cross or intersect with other channels, and in various embodiments they can be substantially parallel to one another. In electrophoresis applications, channels are preferably filled with a separation media.

As used herein, the term "separation media" refers to a media in which an electrophoretic separation of sample components takes place. Separation media typically comprise several components, at least one of which is a charge-carrying component or electrolyte. The charge-carrying component is usually part of a buffer system for maintaining the separation media at a defined pH. Media for separating polynucleotides, proteins, or other biomolecules having different sizes but identical charge-frictional drag ratios in free solution, further include a sieving component. Such sieving component is typically composed of a cross-linked polymer gel, e.g., cross-linked polyacrylamide or agarose, or a polymer solution, e.g., a solution of polyacrylamide, hydroxyethyl cellulose, and the like.

As used herein, the term "sample component" refers to a collection of molecules comprising a subset of a sample in the electrophoresis system. Such a sample component may be passing through a channel in a microfluidic chip or may be exiting or passing from a channel or channel outlet of a microfluidic chip. In this latter case such sample component is referred to as an "eluted sample component." It should be appreciated that any such sample component includes both sample components that elute as discrete peaks or bands and those that elute as a continuous stream. In other words, a sample component or an eluted sample component may be a discrete peak or band comprising components having similar electrophoretic migration velocities, or it may be a longer stream of charged particles or ions passing through or eluting from a channel. It should also be appreciated that the use of the term "component" means either a specific chemical component of the sample or a collection of various chemical components of the sample that elute at the same time. In other words, the term "component" should not be construed as limited to a single chemical species that is part of the sample.

As used herein, the term "distortion" refers to a change in the size, shape, and/or velocity of an eluted sample component, for example, a change in the shape of a sample component upon exiting a microfluidic channel and passing into a detection cell having a larger cross sectional area. Such distortion includes compression and/or expansion of the sample component in the direction of migration, and/or compression and/or expansion of the sample component in a direction normal to a direction of electrophoretic migration. Such distortion also includes mixing of adjacent eluted sample component from adjacent channels and mixing of eluted sample component passing from the same channel. Therefore, distortion may occur in all three dimensions.

As used herein, the terms "confining an eluted sample component," "confinement of an eluted sample component," and the like refer to at least partially reducing any distortion of the sample component. Such confinement may include reducing the expansion or broadening of the sample component along the axis of migration, the expansion of the sample component in a direction normal to the axis of migration (e.g., in a top to bottom direction in a detection cell), or the expansion of a sample component in a lateral direction which may cause mixing with another sample component moving in an adjacent path. Such confinement, may include reducing any one or more of these types of expansion.

Figure 2:
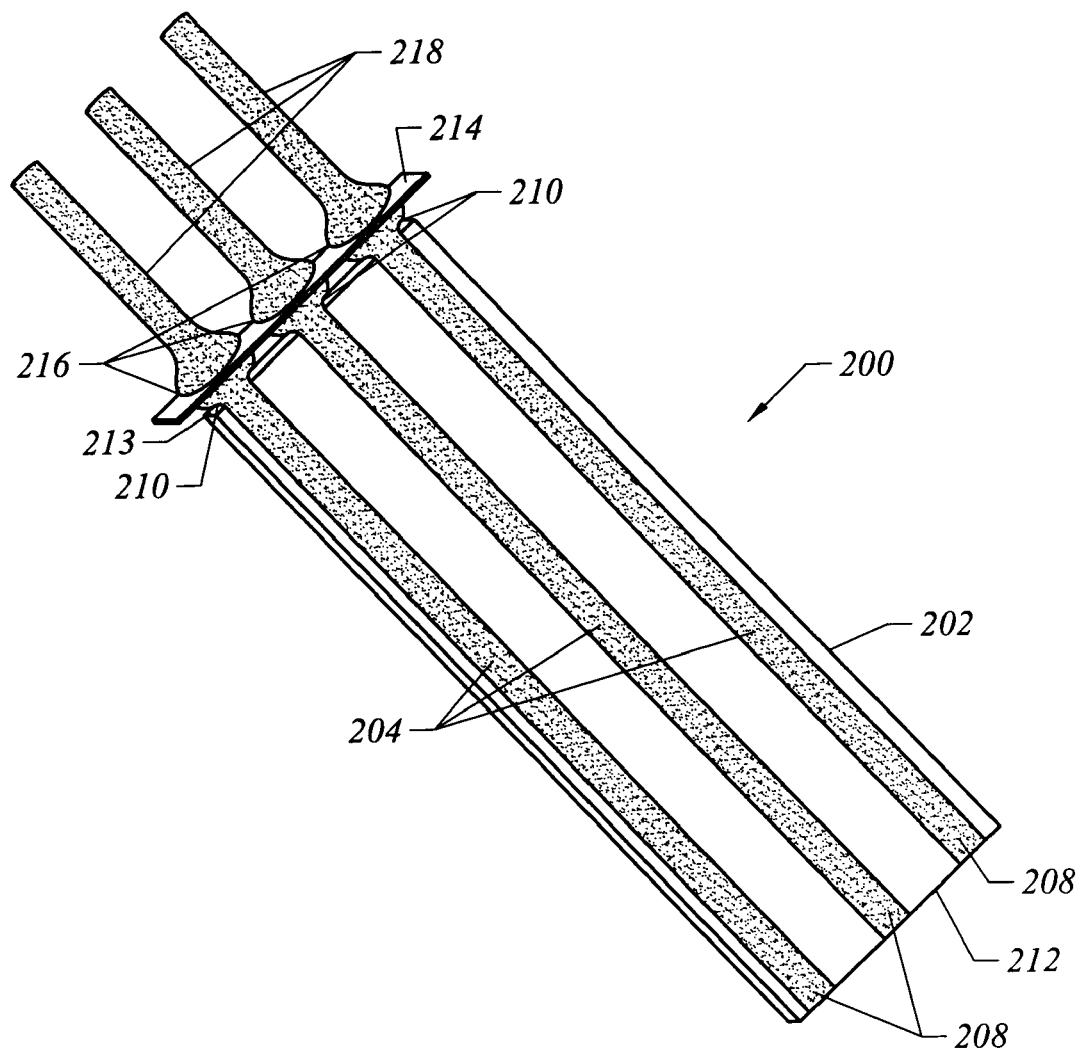
FIG. 2 is a perspective view of a microfluidic chip according to an embodiment of the present teachings.

FIG. 2 is a perspective view of a microfluidic chip according to an embodiment of the present teachings. Microfluidic chip 200 includes a body or substrate 202, a number of channels 204 passing through the substrate 202, and an electrode 214, which is referred to as a "pinching" electrode. The channels 202 preferably extend through chip 200 such that each channel 204 is surrounded by the substrate 202. In this case, the channels 202 are preferably D-shaped with the curved portion of the "D" comprising the bottom of the channel. Alternatively, the channels 204 may be formed as elongated grooves on an upper surface of the chip 200. In either case, the channels 204 are separated from one another by portions of the substrate 202 itself. While three channels 204 are shown for illustrative purposes, one skilled in the art will appreciate that chip 200 can include any number of channels.

It should be appreciated that the geometry of channels can vary widely within the scope of the present teachings. For example, the cross sectional shape of channels may be any shape, including circular, oval, square, rectangular, D-shaped, or any other polygonal shape. Channels may form curved or angular paths through substrate and may be joined or otherwise communicate with other channels or features in the chip. Moreover, the diameter or cross-sectional area may vary within or between channels. Preferbly, the chip 200 comprises approximately 96 to 384 to over 1500 channels 204 with each channel having a D-shape, wherein the curved portion of the D forms the bottom of each channel,and wherein the depth of each channel is approximately 10–200 µm and more preferably approximately 100 µm and the width of each channel is approximately 30–50 µm and more preferably approximately 30 µm.

Each channel 204 includes an inlet 208 and an outlet 210 in fluid communication with the channel 204. The inlets 208 are positioned at the inlet end 212 of the chip 200, and the outlets 210 are positioned at the outlet end 213 of the chip 200. The inlets 208 are configured to accept a predetermined volume of sample, such as a sample containing charged particles to be separated and/or analyzed, from a sample introduction device, such as a pipette, a syringe, or the like, including, for example, an automated delivery system. In some embodiments, inlets are configured to accept or mate with other devices, such as electrodes for creating electrical potentials to drive movement of charged particles, pumps for providing pressure or flow, valves for control or regulation of pressure and/or flow, etc.

Although the inlets 208 are schematically shown in FIG. 2 as openings on an inlet end 212 of the chip 200, one skilled in the art will appreciate that the inlets 208 may be configured in any manner to facilitate introduction of a desired quantity of sample into each channel 204. For example, the inlets 208 may be configured as open ports or wells (not shown) on an upper surface of chip 200, such that each port or well fluidly communicates with at least one channel 204 to provide a passage for samples into that channel. Such inlets 208 can be arranged on an end or the upper surface of chip 200 in any manner or pattern, such as in a row or a matrix.

Preferably, each channel 204 has one corresponding inlet 208 as shown. Alternatively, chip 200 could be configured to have any number of channels 204 and inlets 208 arranged in any configuration, depending upon a desired application. For example, one or more channels 204 could have communicating branches (not shown) to allow introduction of one or more additional samples to be mixed with a primary sample, or to allow fluid communication for controlling pressure or flow, applying an electrical current, etc.

The chip 200 may be composed of any of a wide variety of materials, including, but not limited to, polymers, plastics, silica or silica-based materials, resins, carbon, or inorganic glasses. Because samples are preferably detected outside of the chip after samples elute from the channels, suitable materials include non-optically clear polymers materials, such as TEFLON, silicon, plastics, and the like.

The chip 200 may be fabricated using any suitable process, such as micro-machining, casting, or thermo-forming. The chip 200 may be machined from, or formed or cast into, a single piece of substrate material. Alternatively, the chip 200 may be made of two more sections or plates. For example, a chip according to the present teachings may be comprised of a top plate and a bottom plate, each of which with approximately half-cylinder grooves, such that the channels 204 are formed by mating and securing the two plates.

An electrode 214 is disposed adjacent to the outlets 210 of the channels 204, which may be held in place mechanically by any means known in the art. This electrode is referred to as a "pinching" electrode since, in use, it acts to produce an electrical field capable of confining, in up to three dimensions, sample bands eluting from channels in a microfluidic chip or similar device. The pinching electrode 214 includes one or more holes or passages 216 that allow sample bands or other fluids to pass therethrough. The number and arrangement of passages 216 preferably corresponds with the number and arrangement of outlets 210 of the chip 200. The pinching electrode 214 is located in close proximity to outlet end 213 of chip 200 such that sample bands eluting from each outlet 210 pass through a corresponding passage 216 in the pinching electrode 214. The shape of passages 216 are preferably circular and correspond to the shape of outlets 210. Alternatively, the passages 216may be any shape, e.g., circular, oval, square, rectangular or any other shape, and do not necessarily correspond to the shape of the corresponding outlets 210. Passages 216 are preferably larger than the corresponding outlets 210 as shown in FIG. 2. However, in other embodiments, the passages 216 may be approximately the same size or smaller than outlets 210.

The pinching electrode 214 preferably comprises an electrically conductive material that, when coupled with a power source (not shown), is capable of creating an electrical field that surrounds each of the channel outlets 210. The electrical field is preferably a "pinching field" having sufficient magnitude and polarity to pinch or confine the eluted sample components to a desired sample flow path 218 to avoid distortion or mixing between adjacent eluted sample components after exiting the channels 204. It should be appreciated that the sample flow path 218 is not defined by any physical structure, other than, for example, the outer boundaries (e.g., the top, bottom, and sides) of a detection cell body itself, and is simply the path traversed by an eluted sample component.

As stated above, the passages 216 are preferably holes through the pinching electrode 214 such that the electrode material completely surrounds each passage 216. Accordingly, in use, an electrical field is generated by the electrode 214 that preferably surrounds each channel outlet 210 and forces an eluted sample component passing through each passage 216 towards the center of that passage, thereby confining the sample component to its respective sample flow path 218. For example, in electrophoretic applications, as will be discussed in further detail below, a pair of electrophoresis electrodes (e.g., a cathode and an anode) cause separation of a sample into discrete sample components that pass through the passages 216. As these sample components elute from the chip 200, they pass through the passages 216 and are subject to the electrical field created by the pinching electrode 214. This electrical field tends to force the sample components toward the center of their respective sample flow paths 218, thereby providing three-dimensional confinement of the eluted sample components. More specifically, the tendency of the sample component to expand or broaden in its direction of travel, to expand in a lateral direction such that mixing with an adjacent channel may occur, or to expand in a direction normal to its direction of travel along the channel (i.e., in the direction of the depth of a channel) may each be reduced.

Figure 2A:
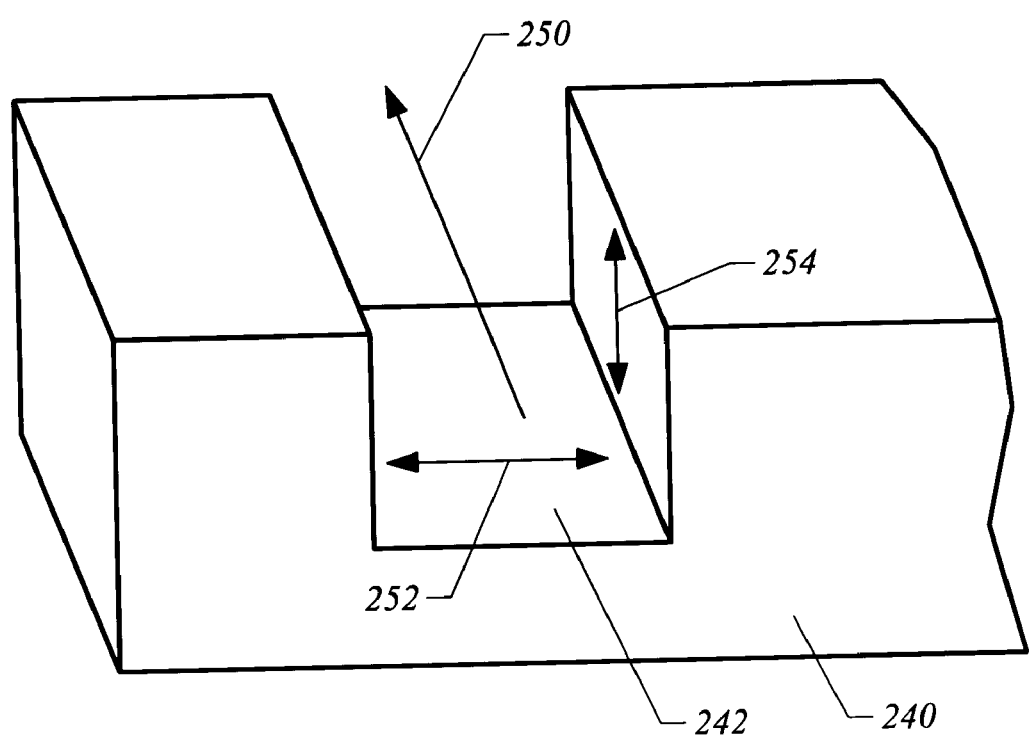
FIG. 2A is a perspective view of a channel to illustrate the various directions in which a sample component may be confined by the present teachings.

FIG. 2A is a perspective view of a channel to illustrate the various directions in which a sample component may be confined by the present teachings or in which the distortion of a sample component may be reduced. A portion of a chip 240 is shown having a channel 242. It should be appreciated that the dimensions of the chip 240 and the channel 242 are not intended to be representative of any actual dimensions or proportions. FIG. 2A is simply used to illustrate the directions in which a sample component may be confined. The direction of migration or travel for a sample component passing through the channel 242 is in the direction of arrow 250. One dimension in which a sample component may be confined is in this direction of travel 250. In other words, a sample component may be confined by reducing its tendency to broaden or lengthen in this direction 250. A second direction in which a sample component may be confined is laterally, which is represented by arrow 252. A third direction in which a sample component may be confined is vertically, or in a top-to-bottom direction, which is represented by arrow 254.

Returning to FIG. 2, it should be appreciated that while the pinching electrode 214 is shown as a single element in FIG. 2, multiple pinching electrodes may be used where a single pinching electrode is disposed around each sample flow path. It should also be appreciated that such confinement of a discrete eluted sample component may also be achieved for eluted sample components that are not discrete and that elute as a continuous stream of charged ions or particles. In other words, the present teachings also are able to provide continuous or constant confinement as such continuous eluted sample components pass from their respective channels.

Figure 6:
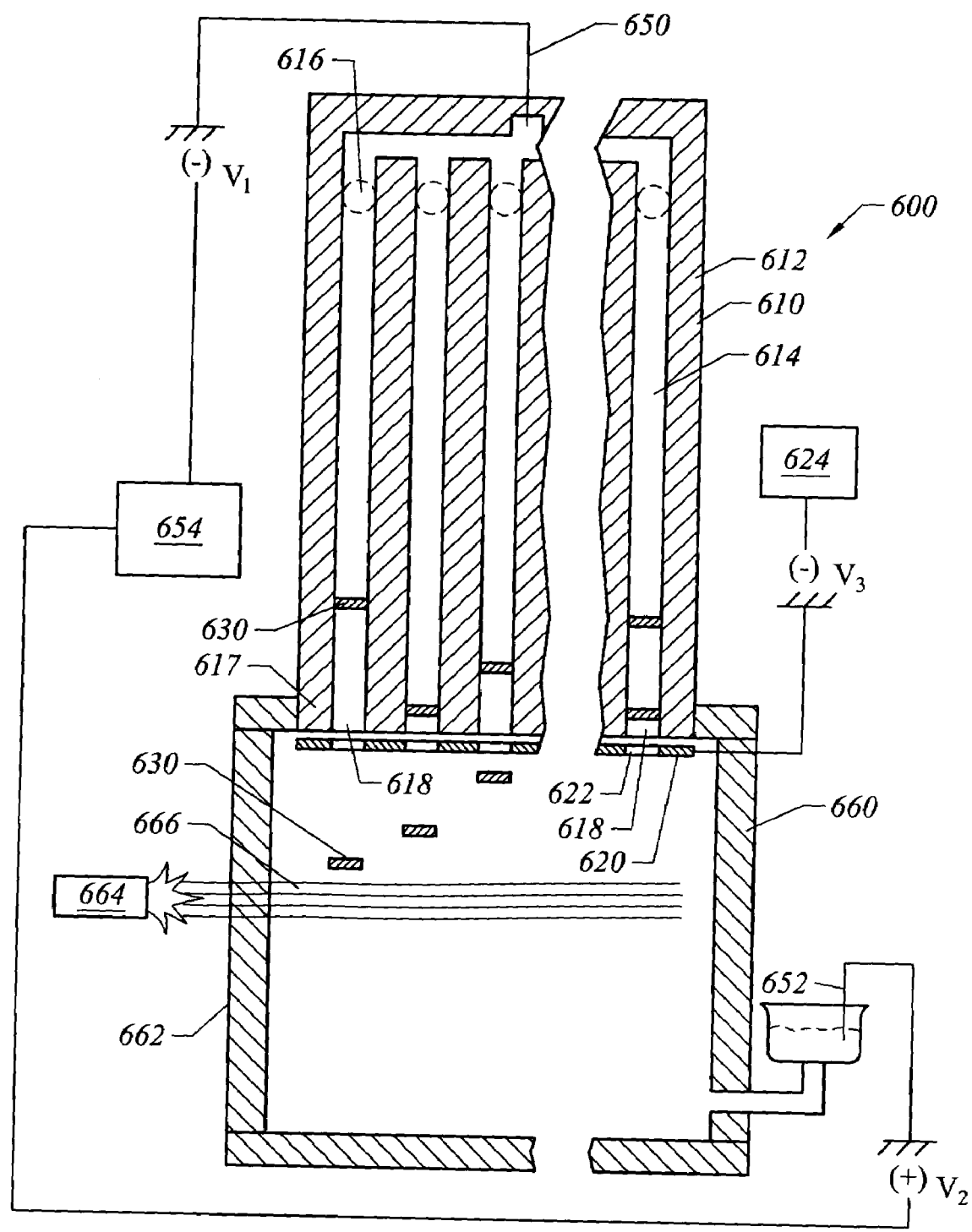
FIG. 6 is a schematic view of an electrophoresis system according to an embodiment of the present teachings.

In an alternative embodiment, solid structures may be used to reduce vertical distortion of sample flow paths such that a pinching electrode need only provide lateral confinement of eluted sample components to prevent distortion or mixing between adjacent sample bands. For example, the pinching electrode may be positioned inside of a detection cell having a solid top and bottom (e.g., the detection cell 660 of FIG. 6, shown as a top view), which act to reduce vertical distortion of the sample flow paths. In such an embodiment, the pinching electrode does not need to completely surround each flow path and may simply be disposed between the sample flow paths to provide lateral confinement to reduce mixing of adjacent sample flow paths. It should be appreciated that multiple pinching electrodes may be used instead of just one. For example, separate pinching electrodes may be used between the sample flow paths.

Similarly, another alternative embodiment utilizes an electrode as described in U.S. Pat. No. 5,833,826 to Nordman to prevent vertical distortion of sample flow paths 218. For example, an electrode in electrical communication with the outlet end 213 of the chip 200 may provide an electrical field around the entire outlet end 213. In such embodiment, the thickness of the chip substrate 202 above and/or below each outlet 210 is preferably relatively thin, e.g., less than about 100 μm and more preferably less than about 40 μm, to optimize the affect of the electrical field.

One skilled in the art will appreciate that applying a voltage to the pinching electrode in an aqueous buffer solution may cause electrolysis of water and consequential generation of hydrogen or oxygen bubbles, depending upon the polarity and magnitude of the voltage applied to the electrodes. To avoid formation of bubbles that may block or impede flow of sample components through passages of the pinching electrode, such is preferably composed of materials, such as palladium, that aid in minimizing the formation of bubbles. U.S. patent application Ser. No. 09/938,947, filed Aug. 24, 2001, entitled "Bubble-Free and Pressure-Generating Electrodes for Electrophoretic and Electroosmotic Devices," incorporated herein in its entirety by reference, discloses suitable materials and methods for making bubble-free electrodes. For example, the pinching electrode 214 may be a palladium metal electrode having a palladium lattice with interstices capable of trapping hydrogen. Such an electrode can be "pre-charged" with stored hydrogen by intermittently reversing its polarity to generate hydrogen through electrolysis of water. The stored hydrogen in turn helps to minimize or prevent the formation of oxygen bubbles when the electrode is used as an anode.

Figure 3:
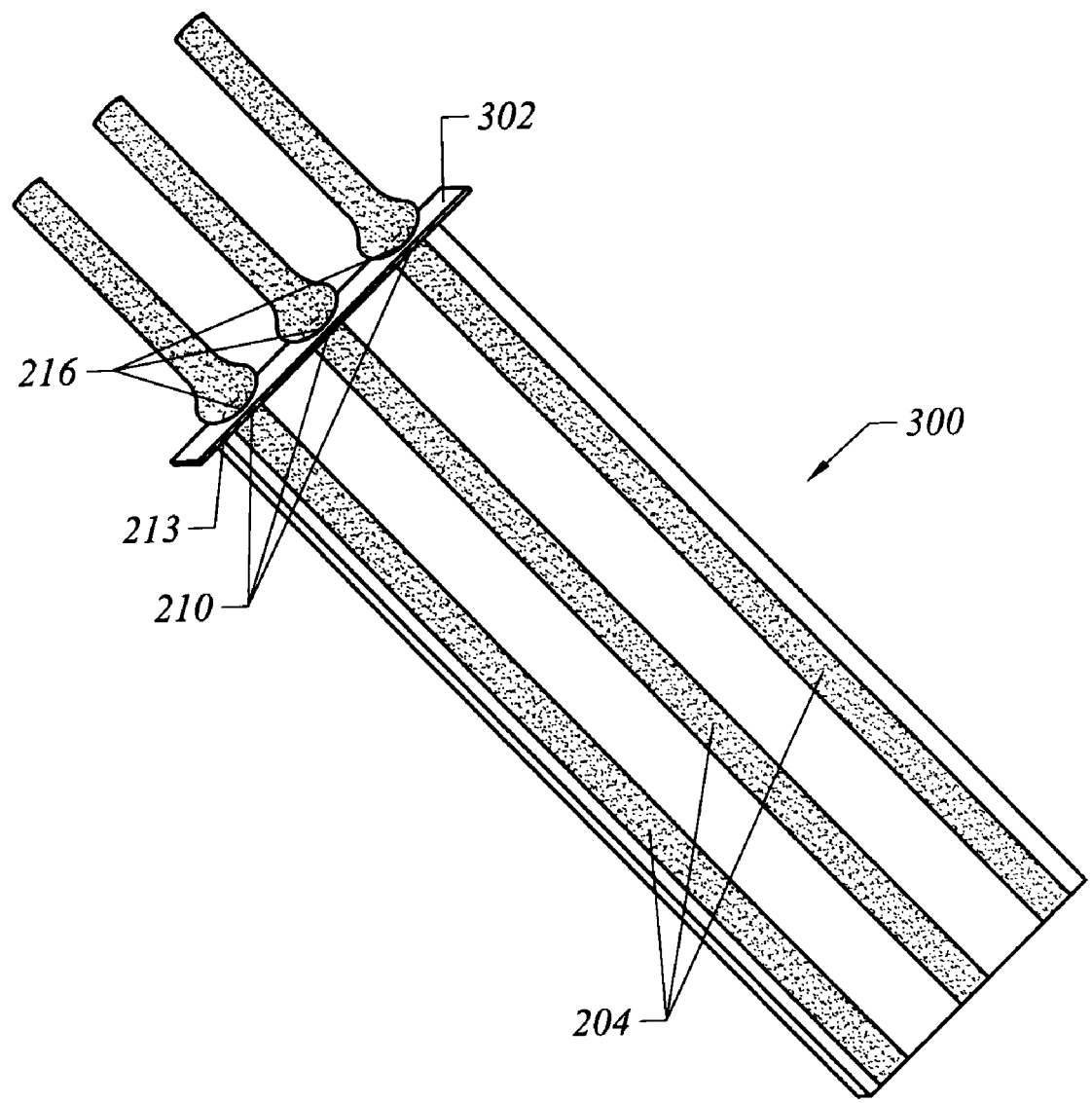
FIG. 3 is a perspective view of a microfluidic chip according to another embodiment of the present teachings.

FIG. 3 is a perspective view of a microfluidic chip according to another embodiment of the present teachings. The microfluidic chip 300 is similar to the microfluidic chip 200 discussed above in connection with FIG. 2, except that a pinching electrode 302 is attached to outlet end 213 of chip 300. As with the pinching electrode 214 of FIG. 2, in this case the pinching electrode 302 includes one or more holes or passages 216 that allow sample components eluting from the channel outlets 210 to pass therethrough. The number and arrangement of passages 216 preferably corresponds with the number and arrangement of the outlets 210 of the chip 300, such that the pinching electrode 302 surrounds each outlet 210. The shape of passages 216 are preferably circular and correspond to the shape of the outlets 210. Alternatively, the passages 216 may be any shape, e.g., circular, oval, square, rectangular or any other shape, and do not necessarily correspond to the shape of the corresponding outlets 210. The passages 216 are preferably the same size as outlets 210; however, the size of passage 216 may be larger or smaller than the size of the corresponding outlets 210. As mentioned above, the pinching electrode 302 is attached to the outlet end 213 of the chip 300, such that samples eluting from the outlets 210 necessarily pass through the corresponding passages 216 in the pinching electrode 302.

The pinching electrode 302 has essentially the same characteristics as the pinching electrode 214 described above in connection with FIG. 2, except for its physical attachment to the chip 300. The pinching electrode 302 may be attached to the chip 300 by any suitable attachment means, including, but not limited to, adhesives, mechanical fasteners, or by friction fitting. Alternatively, the pinching electrode 302 may be formed on the chip 300 through a coating or deposition process. For example, the pinching electrode 302 may be a metalized coating applied to outlet end 213 of the chip 300, e.g. a palladium coating having bubbleless electrode characteristics as described in U.S. patent application Ser. No. 09/938,947. In such embodiments, it may be acceptable for some of the electrode coating material to enter the channels 204, so long as the material does not plug or reduce the flow through the outlets 210. In fact, depending upon the amount of material and the particular application, partially lining the inside surface of the channels 204 near the outlets 210 may provide improved confinement of the sample components eluting from the outlets 210.

Figure 4:
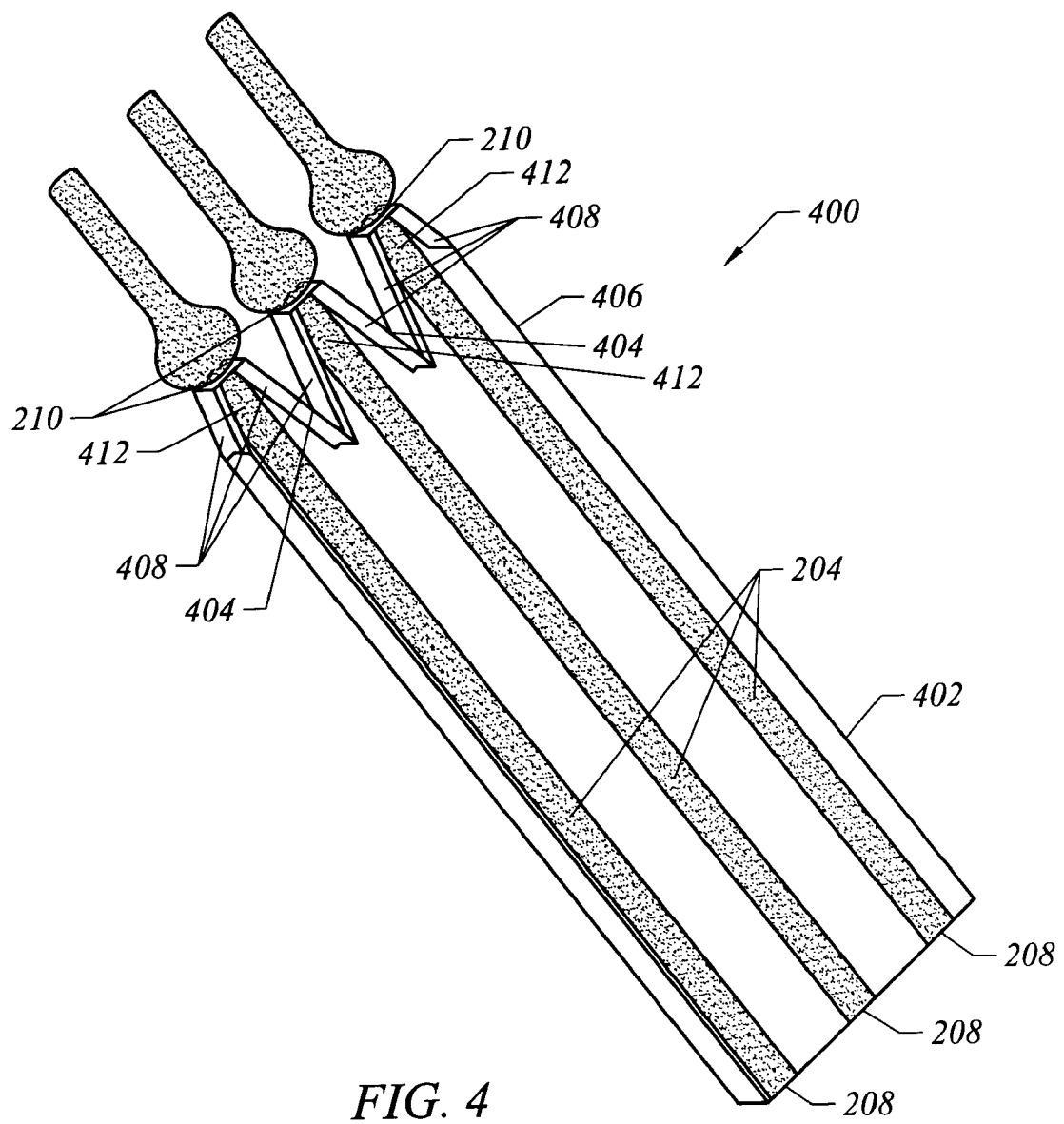
FIG. 4 is a perspective view of a microfluidic chip according to another embodiment of the present teachings.

FIG. 4 is a perspective view of a microfluidic chip according to another embodiment of the present teachings. Similar to the chips shown in FIGS. 2 and 3, the microfluidic chip 400 comprises a substrate 402 having a number of parallel channels 204 therethrough, and each channel 204 includes an inlet 208 and an outlet 210. However, unlike the embodiments described above in connection with FIGS. 2 and 3, the chip 400 in this embodiment includes notches 404 in the outlet end 406 of substrate 402 between each of the channel outlets 210. A pinching electrode 408 is attached to outlet end 406 and conforms to the surface of the notches 404. The pinching electrode 408 may have the same composition and features as the pinching electrodes, 214, 302 described above in connection with FIGS. 2 and 3. For example, the electrode 408 has a number of passages 410, each of which corresponds to a passage outlet 210 of the chip 400.

The pinching electrode 408 may be separately constructed and attached to outlet end 406 by any suitable attachment means, including, but not limited to, adhesives and mechanical fasteners. In some embodiments, the pinching electrode 408 comprises a metalized coating, such as a coating comprising palladium, applied to notches 404 at the outlet end 406 of the chip 400.

In use and similar to the pinching electrodes discussed in connection with FIGS. 2 and 3, the pinching electrode 408 in this embodiment is also attached to a power source (not shown) and provides an electrical field at outlet end 406 of the chip 400 that is capable of creating an electrical pinching field that surrounds each of the channel outlets 210 to pinch or confine the sample components as they elute from the outlets 210. In other words, the electrical field created by the pinching electrode 408 extends around the end portions 412 of each channel 204, which are those portions of the channel created by the notches 404 that extend separately. More specifically, the notches 404 allow the pinching field to more completely surround the channels 204 near the outlet end 406 to further minimize distortion of eluted sample components. As with the chip 302 discussed above in connection with FIG. 3, preferably, the pinching electrode 408 in this embodiment also completely surrounds each channel outlet 210. In some embodiments, however, the electrode 408 covers the notched regions 404 at the outlet end 406 between each channel outlet 210 but does not completely surround each channel. In such embodiments, the substrate 402 above and/or below the outlets 210 is relatively thin to maximize the effect of the pinching field. Alternatively, solid structures positioned, for example, above and/or below the outlets 210, may also prevent distortion of eluted sample components in those directions. Such structures may include flat surfaces that form the top and bottom portions of the chip itself; however, such structures may or may not be integral to the microchip itself.

Figure 5:
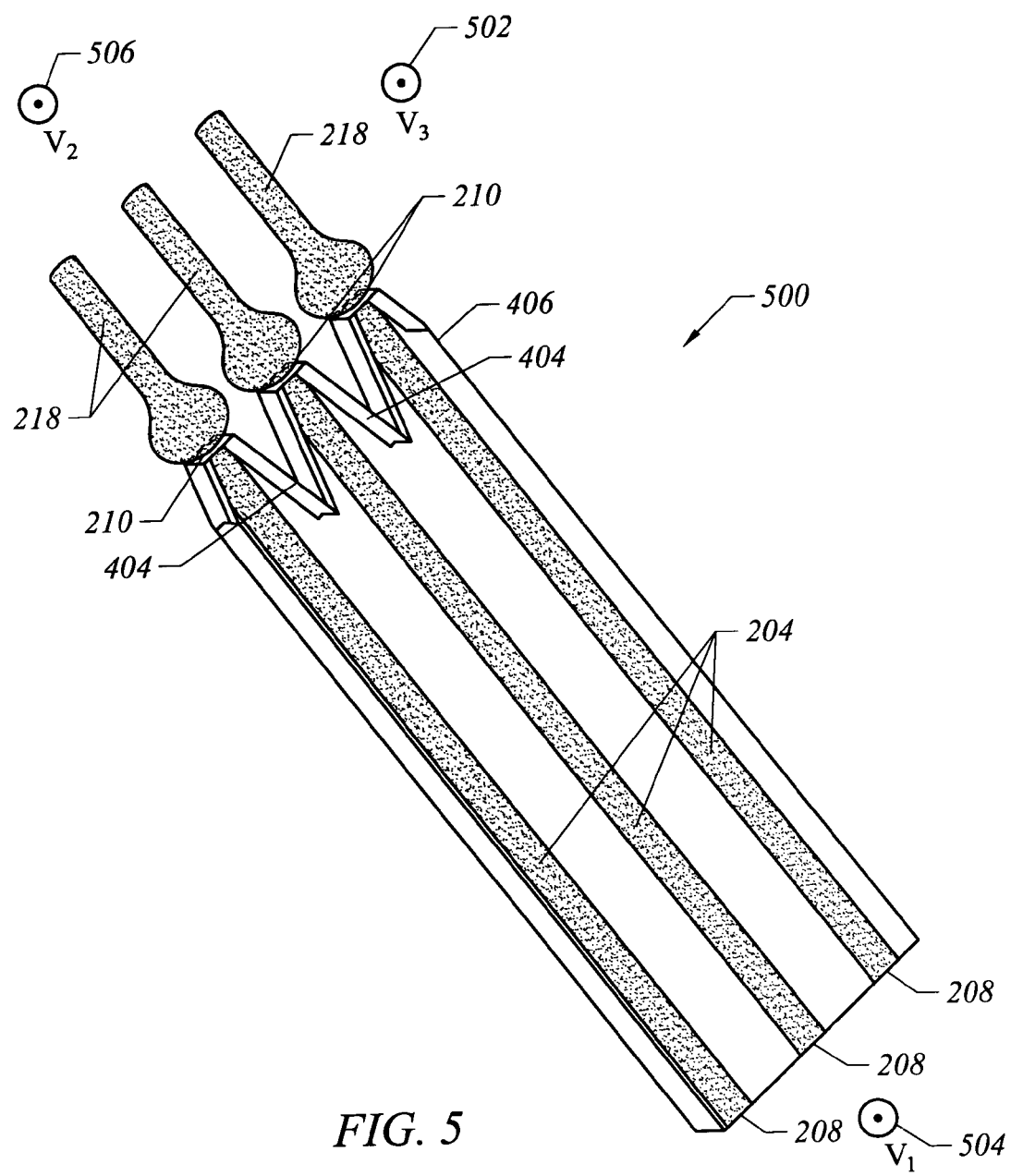
FIG. 5 is a perspective view of a microfluidic chip according to another embodiment of the teachings.

FIG. 5 is a perspective view of a microfluidic chip according to another embodiment of the present teachings. The microfluidic chip 500 in this embodiment is similar to that described in connection with FIG. 4 in that the chip 500 includes notches in an outlet end 406 that separate the outlets 210. However, the chip 500 does not include a pinching electrode that is adjacent or in contact with the chip 500. Rather, an electrode 502, such as that described in U.S. Pat. No. 5,833,826 to Nordman, is simply in fluid communication with the outlet end 406 of the chip 500 and provides an electrical field to reduce distortion of sample flow paths 218. In particular, the notches 404 allow the electrical field from the electrode 502 to surround the channels 204 near the outlet end 406 of the chip 500.

In use, the voltage $V_3$ of the electrode 502 is adjusted to produce an electrical potential around the channel outlets 210 of sufficient magnitude to counteract the diverging electrical field at each channel outlet 210 caused by electrophoresis electrodes 504, 506. For example, suppose that the sample in the channels 204 is negatively charged, and the voltages of electrodes 504 ($V_1$) and 506 ($V_2$) are set at −1000 units and 0 units, respectively, to produce an electrical driving field through the channels 204 to separate a sample into its components and drive them from the inlets 208, through each channel 204, out through the outlets 210 and across a detection cell (not shown). The electrophoresis electrodes 504 and 506 create a driving potential at the outlet end 406 of a particular magnitude, e.g., −300 units. In such a case, the magnitude of the voltage $V_3$ of the electrode 502 is adjusted to provide a an electrical potential of less than −300 units, e.g. −310 units or lower, to prevent divergence of the electrophoresis driving field and distortion of the sample paths 218. U.S. Pat. No. 5,583,826 to Nordman provides a more thorough description of principles of operation of an electrode in an "electro-flow" system.

FIG. 6 is a schematic view of an electrophoresis system according to an embodiment of the present teachings. The electrophoresis system 600 comprises a microfluidic chip 610 having an array of parallel channels 614 passing therethrough, a pinching electrode 620 positioned near an outlet end 617 of a chip 610, a detection cell 660 in fluid communication with the outlet end 618, and a pair of electrophoresis electrodes 650, 652 to separate a sample into sample components and move them through system channels 614. In addition, the system 600 includes a light source 664 for stimulating the sample components eluting from the channels 614 and a detector (not shown) for detection of any emissions from the sample components 630.

The number and arrangement of the channels 614 may vary, depending upon the desired application and the size, shape and thickness of the substrate 612. Each channel 614 includes an inlet 616 and an outlet 618. The inlets 616 are shown as openings or ports on an upper surface of the chip 610. The inlets 616 fluidly communicate with the channels 614 to allow introduction of samples into the channels 614. The inlets may be arranged in any fashion to facilitate sample introduction from a delivery device, such as a syringe or pipette.

In one embodiment particularly suited to high-throughput analyses, the inlets 616 are configured to mate with the outlets from a microtiter plate or other device having multiple sample wells (not shown). In other embodiments, the inlets 616 are configured to received samples and other fluids from a robotically controlled delivery system. In alternative embodiments, the number of inlets does not correspond directly with the number of channels. For example, one inlet may communicate with multiple channels. Conversely, one channel may have multiple inlets, for example to introduce fluids, electrical currents, pressure, or additional samples.

While the channels 614 are shown as straight and parallel tubular structures, they may be any shape and arranged in any configuration through the substrate 612 as described above. For example, the channels 614 may have circular, rectangular or square cross-sectional shapes as described above, and they may form curved or angular paths through the substrate 612, and may cross or intersect other channels. Moreover, the cross-sectional shape may vary between the channels 614, or even within a particular channel. As discussed above, the cross-sectional area of the channels 614 is preferably between about 75 µm and 1000 µm. Any number of channels 614 may be present in the chip 610, e.g., 2, 4, 8 16, 32, 64, 96, 128, 384, 1536, or more. In some embodiments, the channels 614 are not completely surrounded by the substrate 612 and rather are formed as grooves or troughs on one side of the substrate 612. In this case, each channel preferably has a D-shape, wherein the curved portion of the D forms the bottom of each channel and wherein the depth of each channel is approximately 10–200 µm and more preferably approximately 100 µm and the width of each channel is approximately 30–50 µm and more preferably approximately 30 µm.

As with the other embodiments described above, the chip 610 may be composed of any of a wide variety of materials, including, but not limited to, polymers, plastics, silica or silica-based materials, resins, carbon or inorganic glasses. Because the sample components 630 are detected in a detection cell 600 after eluting from the chip 600, suitable chip materials include non-optically clear polymers materials, such as TEFLON, silicon, plastics, and the like. Moreover, the chip 600 may be fabricated using any suitable process as described above.

A first electrophoresis electrode 650 is in electrical communication with the channel inlets 616 and a second electrophoresis electrode 652 is in electrical communication with the channel outlets 618. During operation of the system 600, the first electrophoresis electrode 650 is maintained at a first voltage $V_1$, and the second electrophoresis electrode 652 is maintained at a second voltage $V_2$ using a power supply 654. Alternatively, a separate power supply may be used for each electrophoresis electrode 650, 652. Preferably, the first electrophoresis electrode 650 is physically isolated from the channel inlets 616 as shown in order to prevent bubbles formed at the surface of the electrode from entering the inlets.

A pinching electrode 620 is similar to the pinching electrode 214 discussed in connection with FIG. 2 and includes an array of passages 622 that correspond to the array of outlets 618 of the chip 610. The pinching electrode 620 is positioned in close proximity to the outlet end 617 of the chip 610 such that the sample components 630 eluting from each of the outlets 618 pass through the corresponding passage 622 of the electrode 618. During operation of the device, the pinching electrode 620 is maintained at a third voltage $V_3$ using a power source 624.

The electrophoresis electrodes 650, 652 and the pinching electrode 620, may be formed from any electrically conducting material. Preferably, these electrodes are made from a chemically inert material, e.g., platinum, palladium, and the like. More preferably, these electrodes are made from a material, e.g., palladium, that minimizes the formation of gases at the electrode surface. Most preferably, the pinching electrode 620 is a bubble-free electrode such as those described previously.

The electrically conductive solution used to establish electrical continuity throughout the system 600 may be any fluid capable of transporting an electrical current. Preferably, the conductive solution is an ionic solution, e.g., an aqueous solution containing a dissolved salt. The ionic strength of the solution is preferably chosen to be high enough to mask ion depletion of the solution in the vicinity of the electrodes but not so high as to cause excessive Joule heating. Such Joule heating is particularly disadvantageous in the detector cell 660 where thermal convection may lead to mixing of neighboring eluted sample components 630. Preferably, the conductive solution includes a buffer for stabilizing the pH of the solution. More preferably, the ionic composition of the conductive solution is the same throughout the system 600.

The detection cell 660 is positioned to receive sample components 630 as they elute from the channels 614 and pass through the passages 622. The detection cell 660 may be fabricated from any suitable electrically insulating material, e.g., glass, plastic, ceramic, and the like. Preferably, to facilitate excitation and optical detection of the eluted sample components 630, part or all of the detection cell 660 is formed from a material that efficiently transmits light, such as glass, quartz, and the like. Preferably, the detection cell 660 is of such composition and configuration so as to minimize the scattering of light and intrinsic fluorescence. In a particularly embodiment, the inside surfaces of the detector cell 660 do not support electroosmotic flow in the presence of an ionic solution and an electric field, e.g., they may be coated with an electroosmotic suppression agent. Other various embodiments of detection cells with improved optical characteristics are described in U.S. patent application U.S. patent application Ser. No. 09/812,750, referred to above.

In use, the channels 614 and the detection cell 660 of system 600 are filled with an electrically conductive media, and a sample or samples of interest are deposited into each channel inlet 616. The magnitude of the voltages of each of the electrophoresis electrodes 650, 652, also referred to as driving electrodes, are adjusted to cause the sample to concurrently separate into respective sample components of charged particles 630 and move from the inlets 616 to and through the outlets 618. The voltage of the pinching electrode 620 is adjusted to confine the sample components 630 passing through the passages 622 in pinching electrode 620, thereby reducing distortion and interference between adjacent eluted sample components as discussed above.

The electrical potential of the pinching electrode 620 will depend on a number of factors including the relative size and shape of each outlet 618, the voltages $V_1$ and $V_2$ of the electrophoresis electrode 650, 652 respectively, and the length, size, and configuration of the channels 614. The length, size, and configuration of the channels 614 is important as these affect the electrical resistance of the channels 614, which, in turn, affects the electrical potential of the driving field at the channel outlets 618.

In the case where the first electrophoresis electrode 650 is the anodic electrode (i.e., it is adjusted to a relatively positive value with respect to the second electrophoresis electrode 652), the magnitude of the voltage of the pinching electrode 620 $V_3$ is preferably set such that it is larger than the electrical potential at the outlet end 617 of chip 610. Conversely, when the first electrophoresis electrode 650 is the cathodic electrode, the magnitude of the voltage $V_3$ of the pinching electrode 620 is preferably set such that $V_3$ is smaller than the electrical potential at the outlet end 617 of the chip 610. Preferably, $V_3$ is adjusted to avoid excessive Joule heating in detection cell 660.

The system of FIG. 6 further includes a detector (not shown) for detecting the sample components eluted into the detection cell 660. The detector may be any type of detector for detecting emission of or absorbance of any type radiation, e.g., radioactivity, fluorescence, UV absorbance, and the like. Preferably the detector is capable of detecting fluorescence from a plurality of locations independently and simultaneously, e.g., a CCD camera, an array of photomultiplier tubes, a diode array, and the like. The detector is connected to a computer to store, analyze, and display data collected by the detector and/or to control the operation of the detector. When fluorescence is used to detect the sample bands, the device also includes a light source 664 for exciting the fluorescence. In a particular embodiment of the system of the present teachings, the light source is a laser, e.g., an argon ion laser, a frequency-doubled solid state laser, and the like.

The following Examples are presented to further illustrate the present teachings and are not deemed to be limiting.

EXAMPLE 1

Figure 7A:
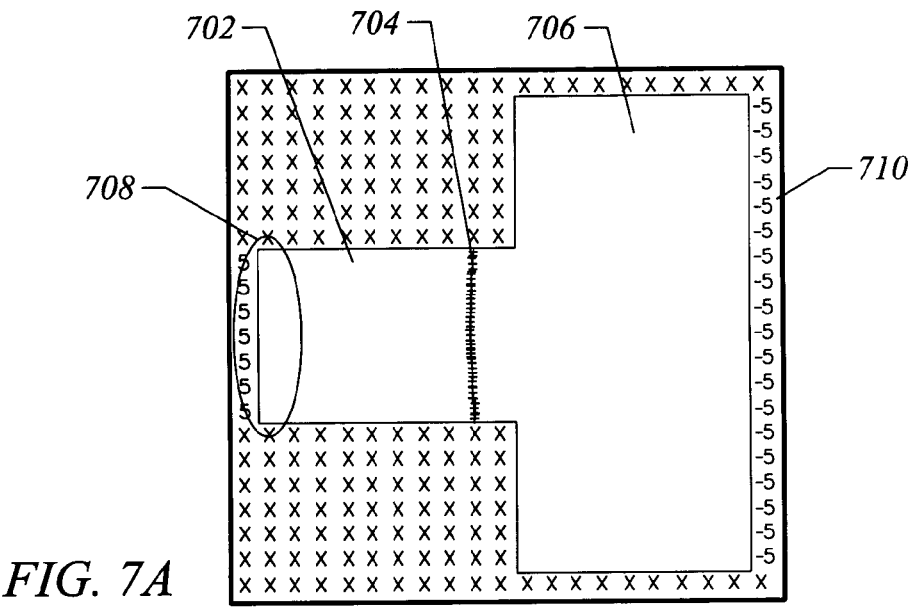
FIGS. 7A–7C illustrate computer simulations of a sample band eluting from a channel in a microfluidic chip into a detection cell.
Figure 7B:
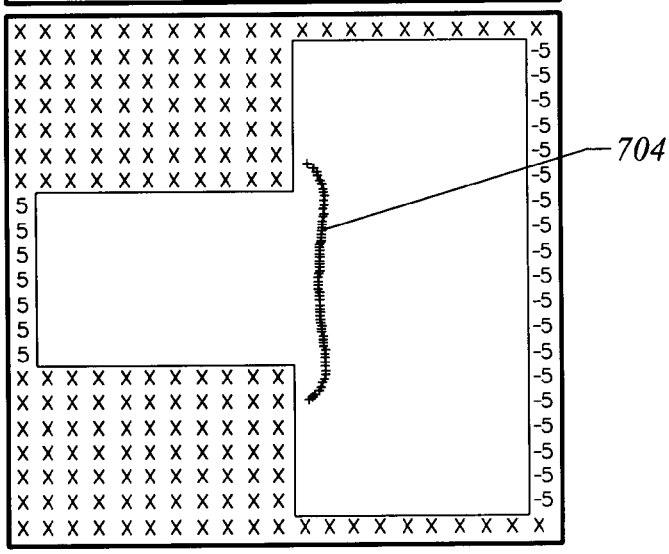
Figure 7C:
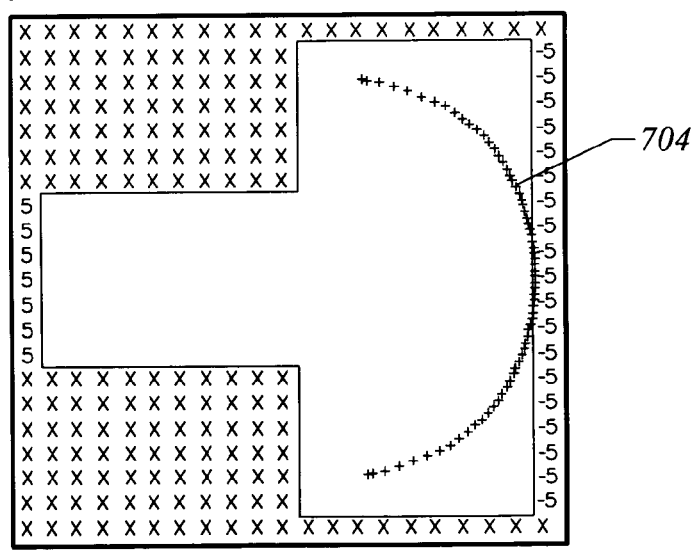

FIGS. 7A–7C illustrate computer simulations of a sample component eluting from a channel in a microfluidic chip into a detection cell. Specifically, FIGS. 7A–7C illustrate distortion of a sample component without benefit of the present teachings. FIG. 7A illustrates a channel 702, a sample component 704, and a detection cell 706. As shown, this simulation was conducted using a first electrophoresis electrode providing a voltage 708 of 5 volts on the channel side and a second electrophoresis electrode providing a voltage 710 of –5 volts on the detection cell side. The "X"s in FIGS. 7A–7C simulate the walls of the channel 702 and the detection cell 706. As shown in FIG. 7A, the sample component 704 is within the channel 702 and is moving toward the detection cell 706. In FIG. 7B, the sample component 704 has eluted from the channel 702 and is within the detection cell 706. Notably, the eluted sample component 704 is beginning to distort compared to its size within the channel 702. In FIG. 7C, the sample component 704 is significantly distorted, thereby making detection more difficult and also increasing the chance for mixing with an adjacent eluted sample component or sample flow path (not shown).

EXAMPLE 2

Figure 8A:
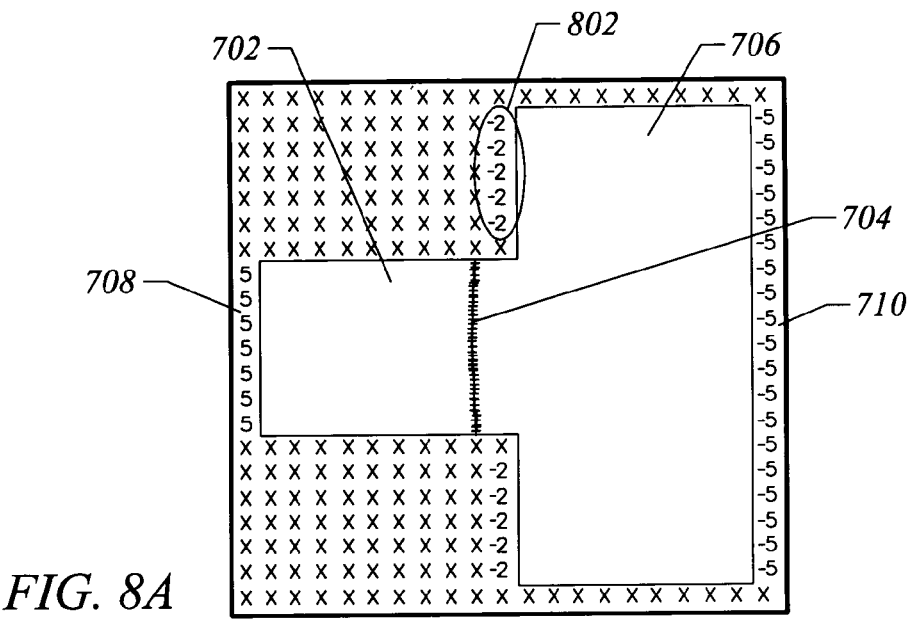
FIGS. 8A–8C illustrate computer simulations of a sample band eluting from a channel in a microfluidic chip into a detection cell according to one embodiment of the present teachings.
Figure 8B:
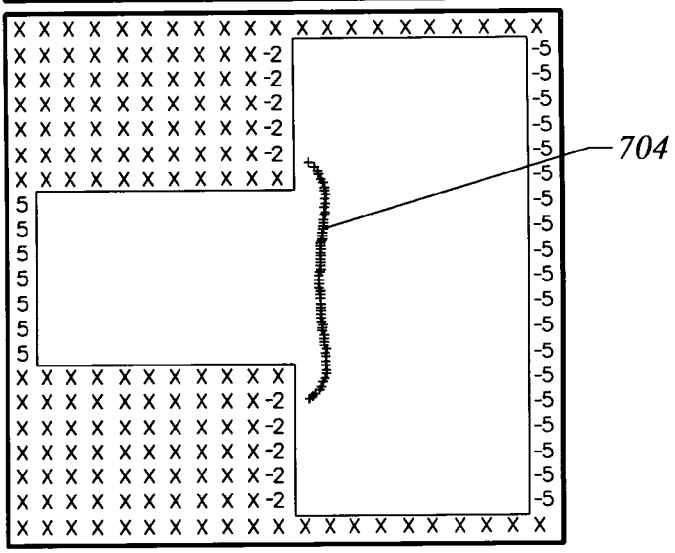
Figure 8C:
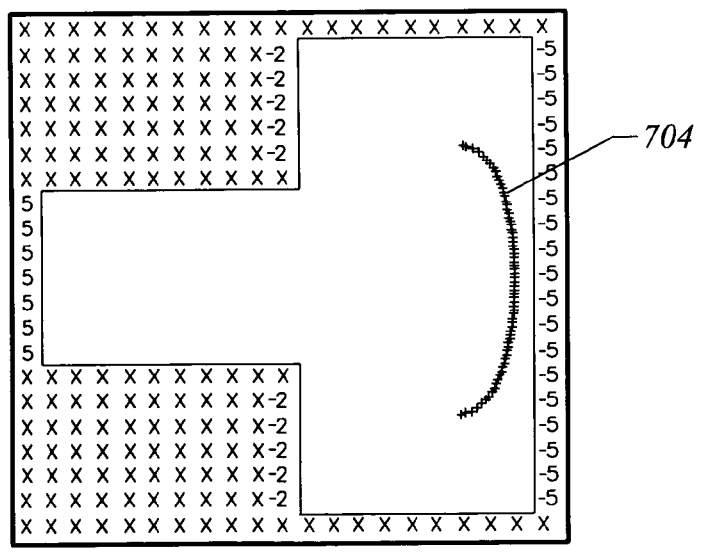

FIGS. 8A–8C illustrate computer simulations of a sample component eluting from a channel in a microfluidic chip into a detection cell according to one embodiment of the present teachings. Specifically, FIGS. 8A–8C illustrate the effect of a pinching electrode on the distortion of an eluted sample component. FIG. 8A illustrates a channel 702, a sample component 704, and a detection cell 706. As shown, this simulation was also conducted using a first electrophoresis electrode providing a voltage 708 of 5 volts on the channel side and a second electrophoresis electrode providing a voltage 710 of –5 volts on the detection cell side. This simulation, however, illustrates the use of a pinching electrode 802 adjacent to the channel outlet 804 (i.e., at the channel tip), wherein the pinching electrode 802 provides a voltage of –2 volts. It should be appreciated that this simulation illustrates the general affect of the present teachings and is not indicative of any particular physical embodiment of a pinching electrode. However, it should be appreciated that the pinching electrode 802 in this simulation is not immediately adjacent to the channel 702 as indicated by the present of an "X" between the pinching electrode voltage as shown and the channel 702.

As shown in FIG. 8A, the sample component 704 is within the channel 702 and is moving toward the detection cell 706. In FIG. 8B, the sample component 704 has eluted from the channel 702 and is within the detection cell 706. Notably, the eluted sample component is somewhat distorted and expanded compared to its size in the channel 702 or immediately outside of the channel 702 in the detection cell 706. However, the reduction in the amount of expansion of the sample component 704 compared to FIG. 7C is significantly less, which should result in better detection and less chance for mixing with an adjacent eluted sample component or sample flow path.

EXAMPLE 3

Figure 9A:
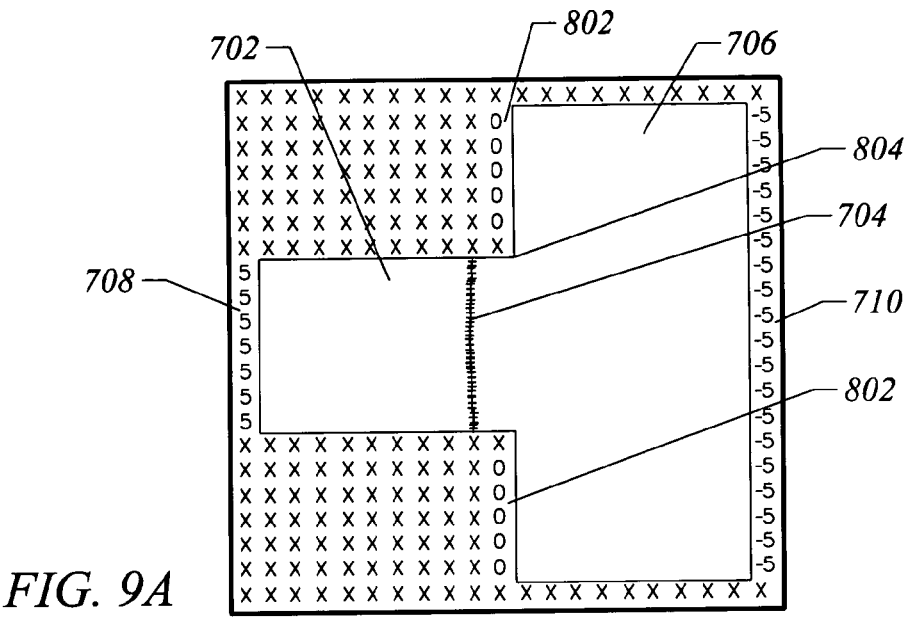
FIGS. 9A–9C illustrate computer simulations of a sample band eluting from a channel in a microfluidic chip into a detection cell according to another embodiment of the present teachings.
Figure 9B:
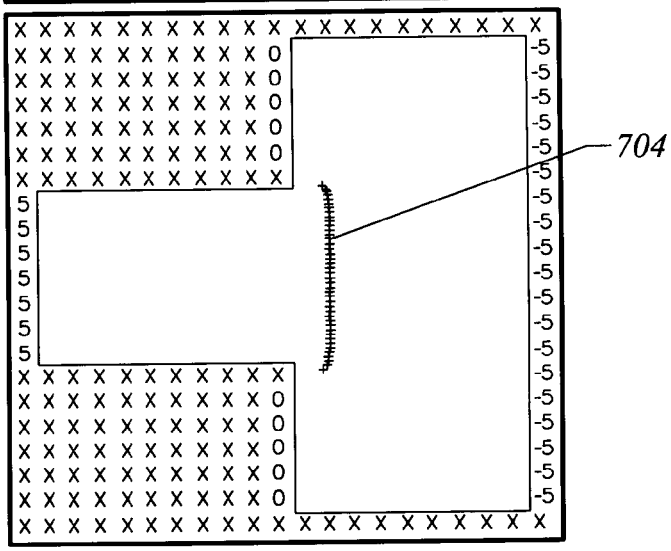
Figure 9C:
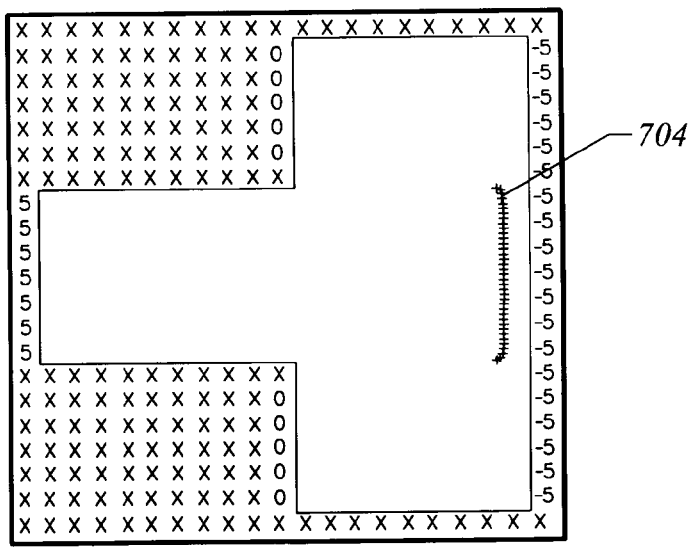

FIGS. 9A–9C illustrate computer simulations of a sample component eluting from a channel in a microfluidic chip into a detection cell according to another embodiment of the present teachings. Specifically, FIGS. 9A–9C are identical to FIGS. 8A–8C except that the pinching electrode 802 now provides a voltage of 0 volts. In this case, the electrode is referred to as a "floating electrode," wherein the potential of the electrode will be the same as the potential at that point in the channel or detection cell based upon the voltage applied in the electrophoresis separation. In other words, no potential is separately applied and the electrode simply assumes the same potential that exists in the matrix at that point. As shown, the expansion and distortion of the eluted sample component 704 is even less in this Example compared to Example 2.

EXAMPLE 4

Figure 10A:
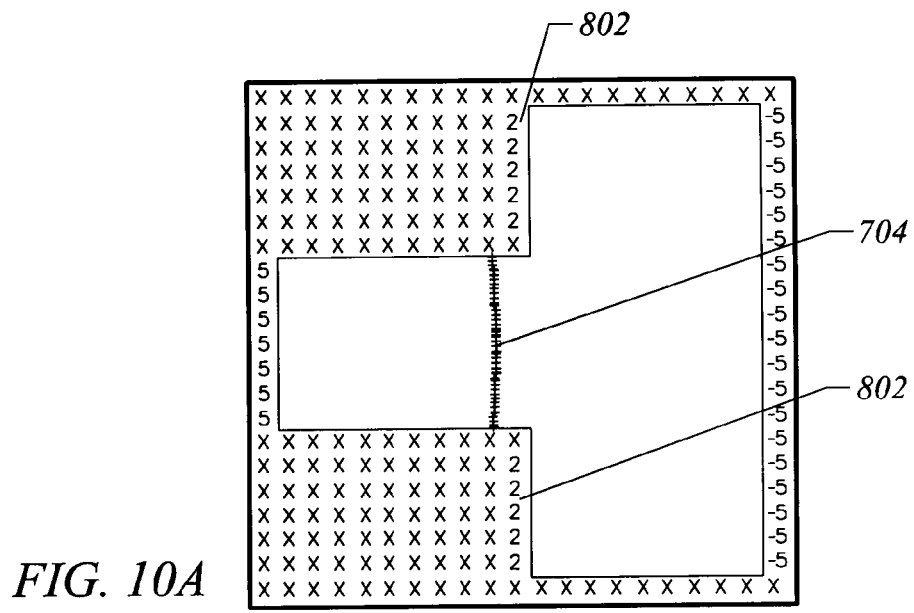
FIGS. 10A–10C illustrate computer simulations of a sample band eluting from a channel in a microfluidic chip into a detection cell according to another embodiment of the present teachings.
Figure 10B:
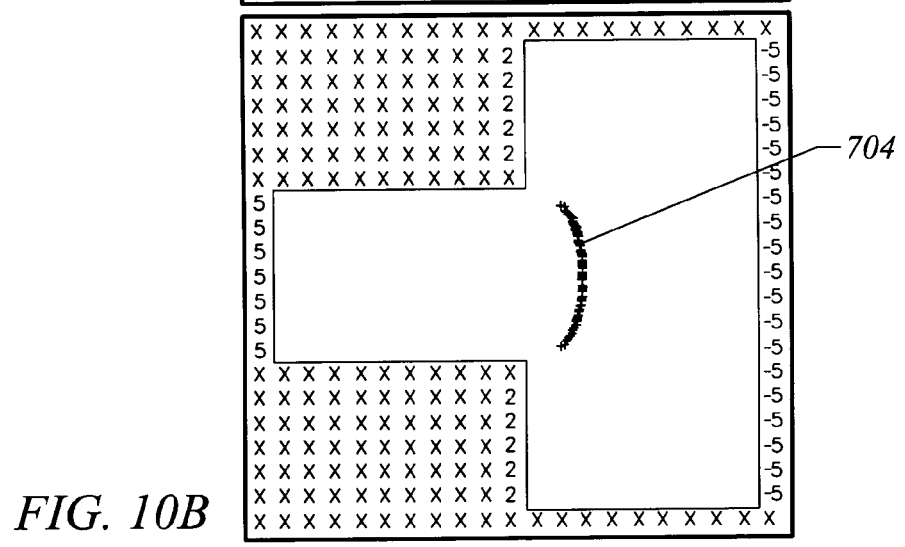
Figure 10C:
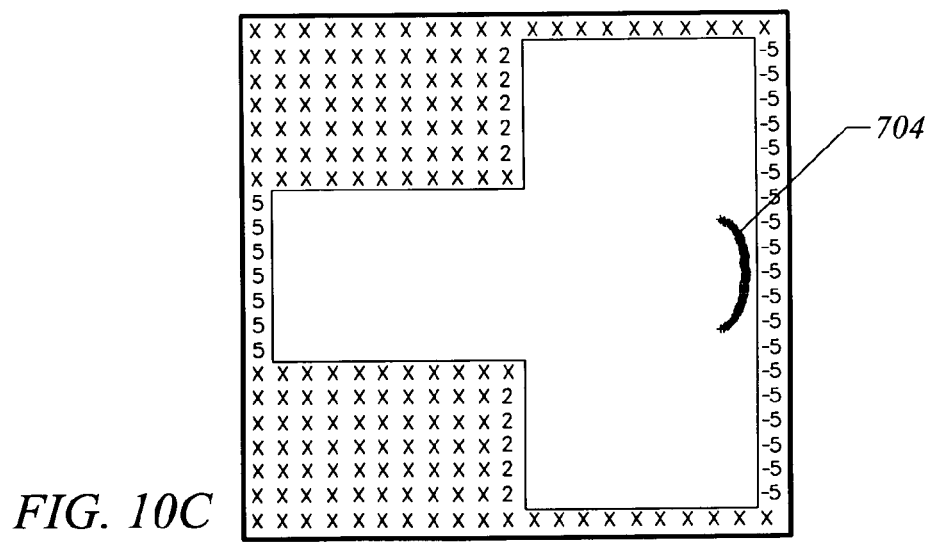

FIGS. 10A–10C illustrate computer simulations of a sample component eluting from a-channel in a microfluidic chip into a detection cell according to another embodiment of the present teachings. Specifically, FIGS. 10A–10C are identical to FIGS. 8A–8C and FIGS. 9A–9C except that the pinching electrode 802 now provides a voltage of –2 volts. As shown, the expansion and distortion of the eluted sample component 704 is now significantly less and is actually compressed compared to its size in the channel 706.

EXAMPLE 5

Figure 11A:
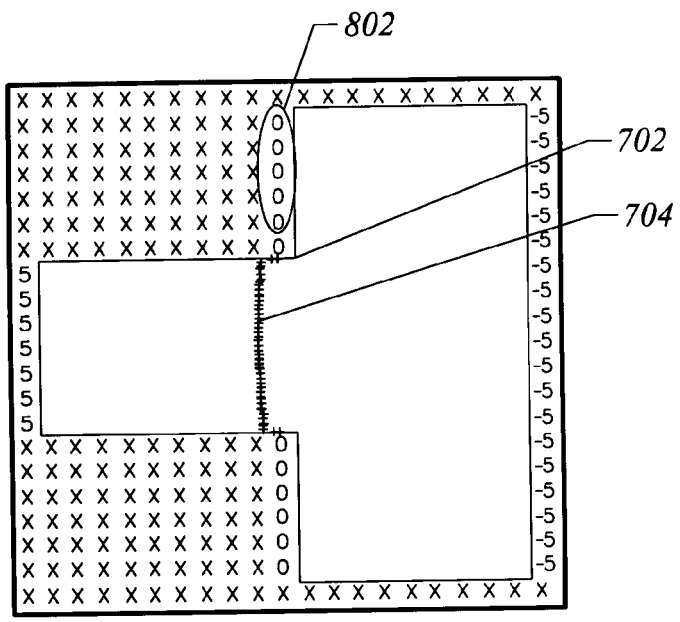
FIGS. 11A–11C illustrate computer simulations of a sample band eluting from a channel in a microfluidic chip into a detection cell according to another embodiment of the present teachings.
Figure 11B:
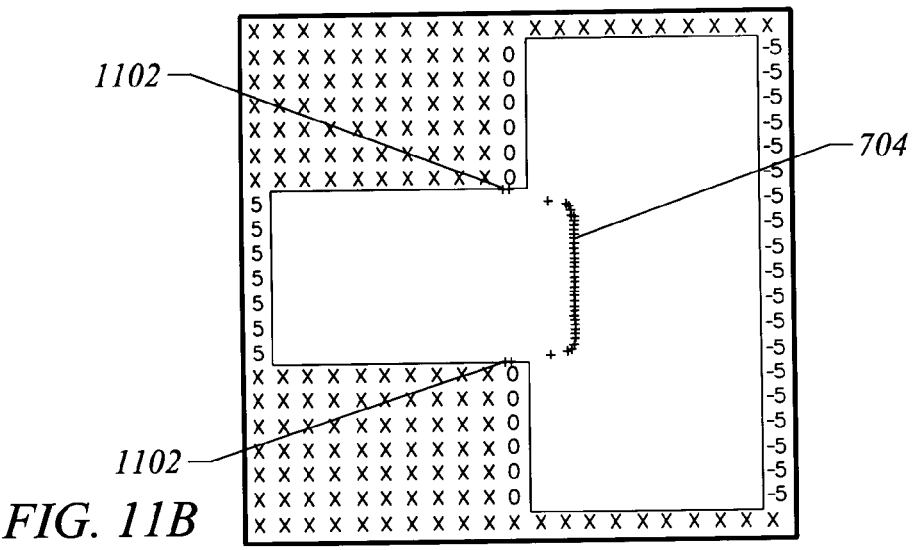
Figure 11C:
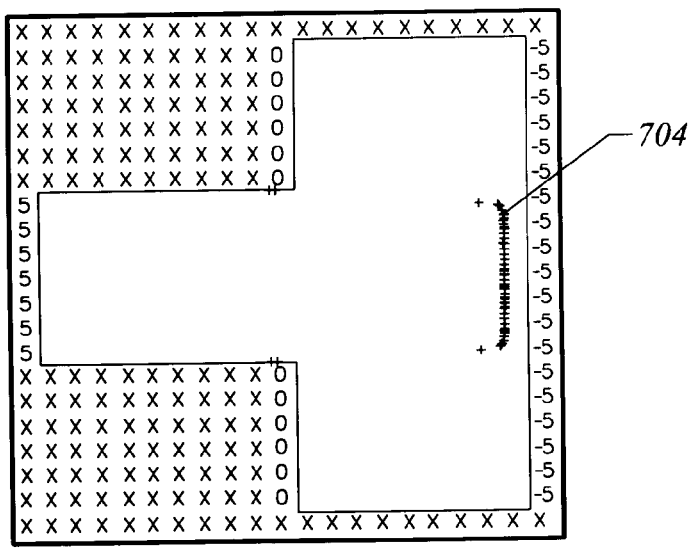

FIGS. 11A–11C illustrate computer simulations of a sample component eluting from a channel in a microfluidic chip into a detection cell according to another embodiment of the present teachings. Specifically, FIGS. 11A–11C are identical to FIGS. 9A–9C except that the pinching electrode 802 is now immediately adjacent to the channel 702 as indicated by the lack of an "X" between the voltage of the pinching electrode 802 and the channel 702. In this Example, the pinching electrode 802 is providing a voltage of 0 volts. In this case, a portion 1102 of the eluted sample component 704 actually attaches to the wall of the channel 702 while the remainder of the sample component elutes from the channel 702, noting that the eluted sample component 704 does not expand significantly in the detection cell 706.

EXAMPLE 6

Figure 12A:
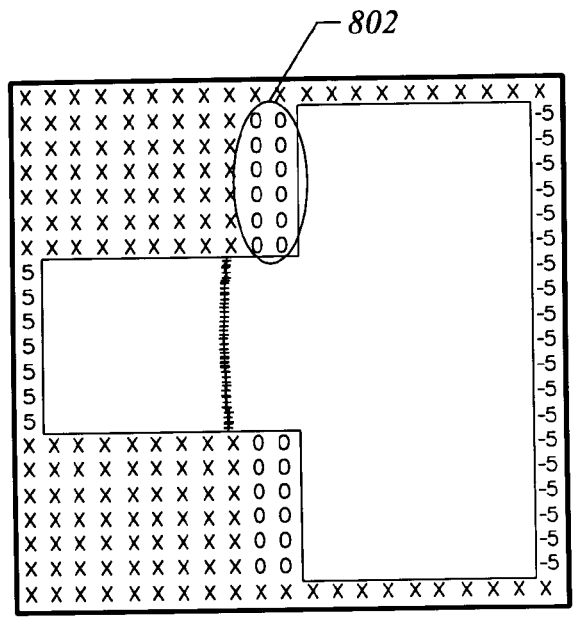
FIGS. 12A–12C illustrate computer simulations of a sample band eluting from a channel in a microfluidic chip into a detection cell according to another embodiment of the present teachings.
Figure 12B:
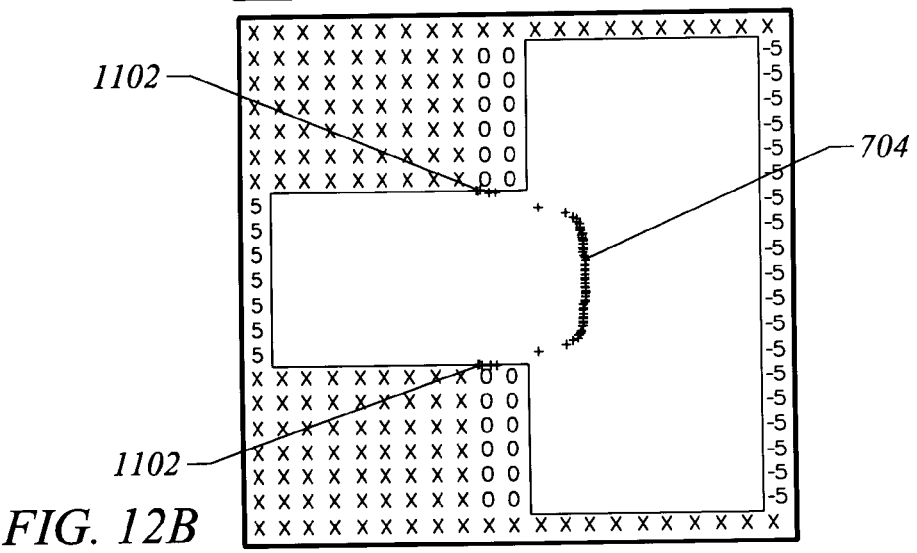
Figure 12C:
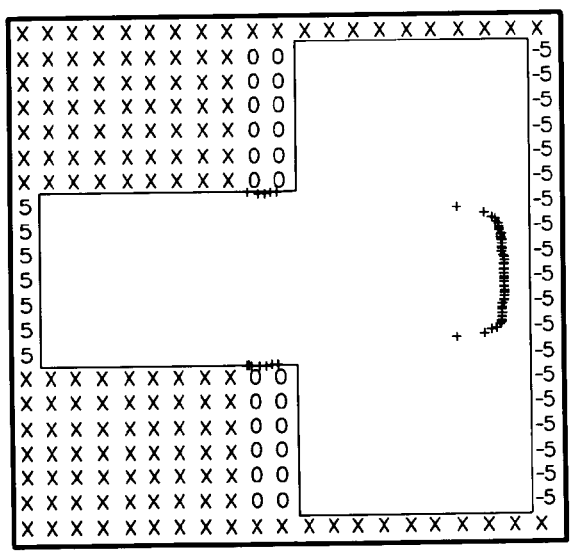

FIGS. 12A–12C illustrate computer simulations of a sample component eluting from a channel in a microfluidic chip into a detection cell according to another embodiment of the present teachings. Specifically, FIGS. 12A–12C are identical to FIGS. 11A–11C except that the pinching electrode 802 is now thicker and is adjacent to a larger portion of the channel wall 702 as illustrated by a second row of "0"s simulating the pinching electrode 802. In this Example, the pinching electrode 802 is providing a voltage of 0 volts. In this case, a greater portion 1102 of the sample component 704 actually attaches to the wall of the channel 702 compared to the simulation of Example 5; however, the remainder of the eluted sample component 704 actually compresses as it elutes from the channel 702.

EXAMPLE 6

Figure 13A:
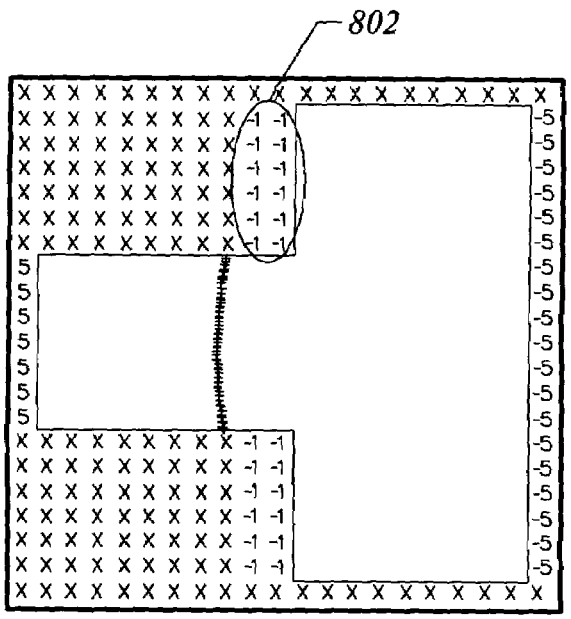
FIGS. 13A–13C illustrate computer simulations of a sample band eluting from a channel in a microfluidic chip into a detection cell according to another embodiment of the present teachings.
Figure 13B:
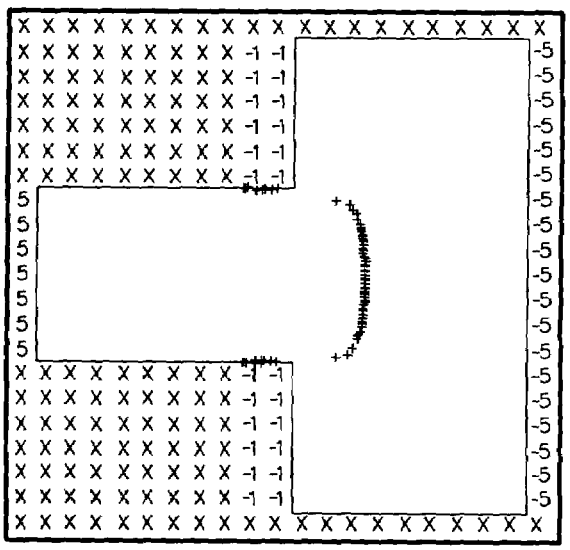
Figure 13C:
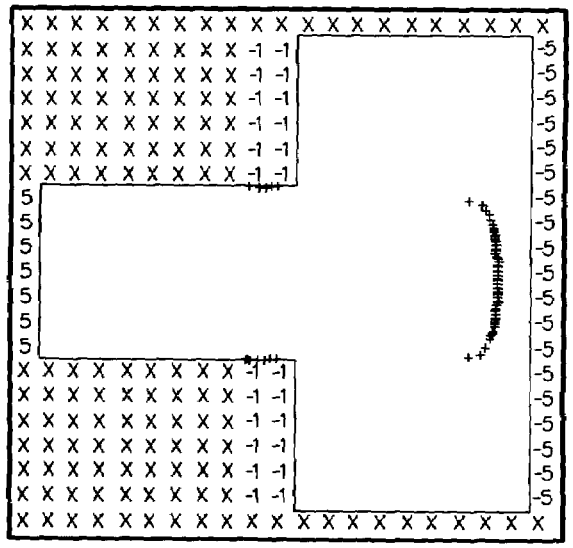

FIGS. 13A–13C illustrate computer simulations of a sample component eluting from a channel in a microfluidic chip into a detection cell according to another embodiment of the present teachings. Specifically, FIGS. 13A–13C are identical to FIGS. 12A–12C except that the pinching electrode 802 is providing a voltage of –1 volts. In this case, a greater even portion of the sample component 704 actually attaches to the wall of the channel 702 compared to the simulation of Example 6; however, the remainder of the eluted sample component 704 also compresses as it elutes from the channel 702.

EXAMPLE 7

Figure 14:
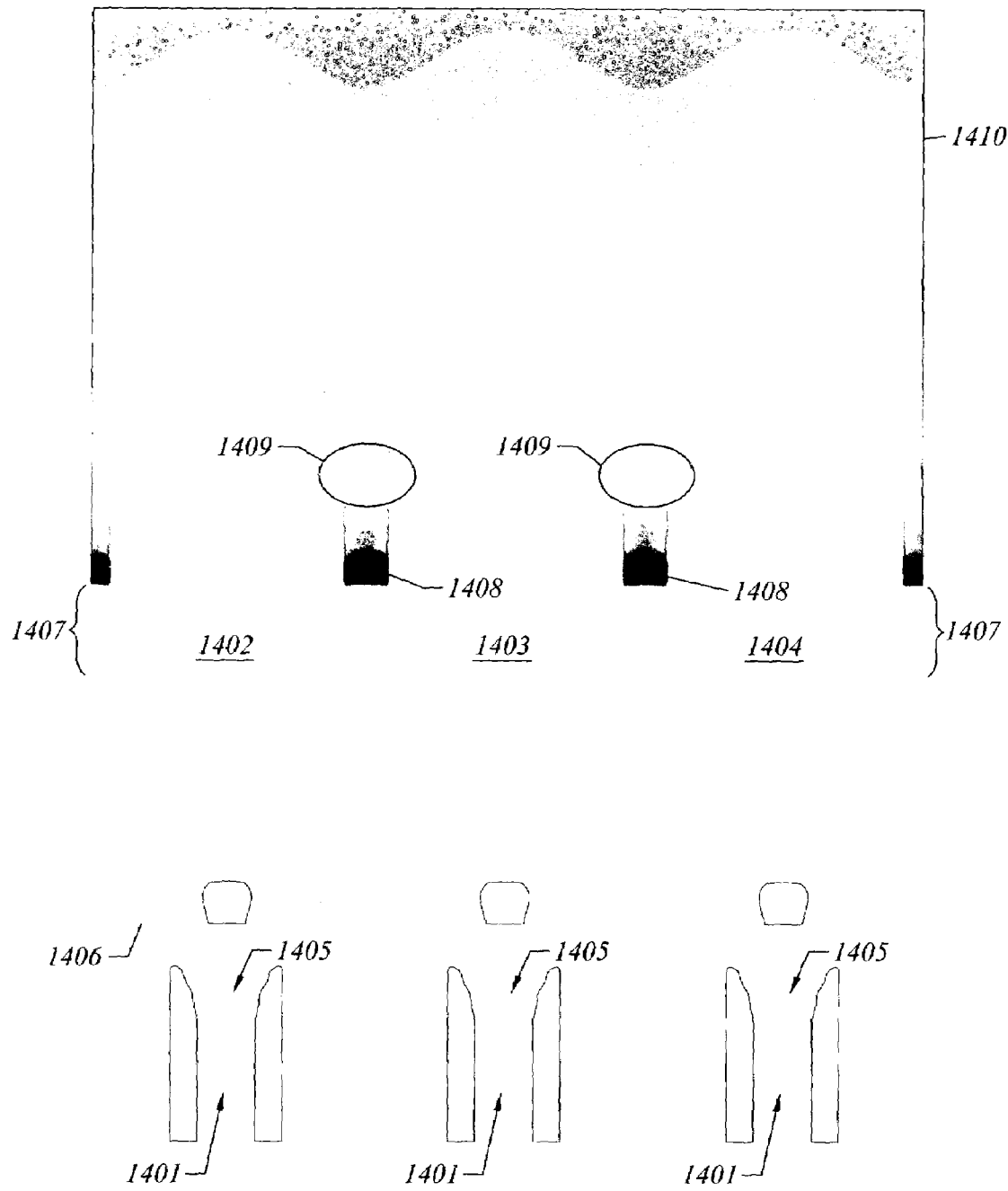
FIG. 14 illustrates a computer simulation of a DNA sample component eluting from a channel in a microfluidic chip into a detection cell according to another embodiment of the present teachings.

FIG. 14 illustrates a computer simulation of a DNA sample component eluting from a channel in a microfluidic chip into a detection cell according to another embodiment of the present teachings. Specifically, FIG. 14 illustrates a top view of three channels (D-shaped) 1401 from which sample components 1402, 1403, 1404 have eluted into detection cell 1404. The outlet end of the channels 1405 is positioned adjacent to the inlet side 1406 of the detection cell 1404 and the sample components 1402, 1403, 1404 move essentially from the bottom of the page to the top of the page. A floating electrode 1407 (shown only as a space that traverses the width of the detection cell 1404) is positioned a given distance from the outlet 1405 of the channels 1401. In this simulation, the floating electrode 1407 assumes the potential present at that point in the detection cell as supplied by the electrophoresis electrodes (not shown). In other words, the floating electrode 1407 does not have a separately applied voltage.

The concentration of each of the sample components is shown by the various levels of shading. A very dark area indicates little or no sample component, while no shading or light shading indicates a concentrated sample component. As shown, the eluted sample components 1402, 1403, 1404 upon exiting from their respective channels 1401 tend to distort and spread out in a horizontal direction. However, upon passing through the floating electrode 1407, the eluted sample components are separated from one another near the floating electrode 1407 as shown by the dark areas 1408 between the sample components or plumes. In other words, near the floating electrode 1407, the sample distortion appears to have been maintained. However, the eluted sample components experience further distortion and mixing downstream of the floating electrode 1407 as indicated by the overlapping of each of the sample components in the more lightly shaded areas (e.g., 1409).

EXAMPLE 8

Figure 15:
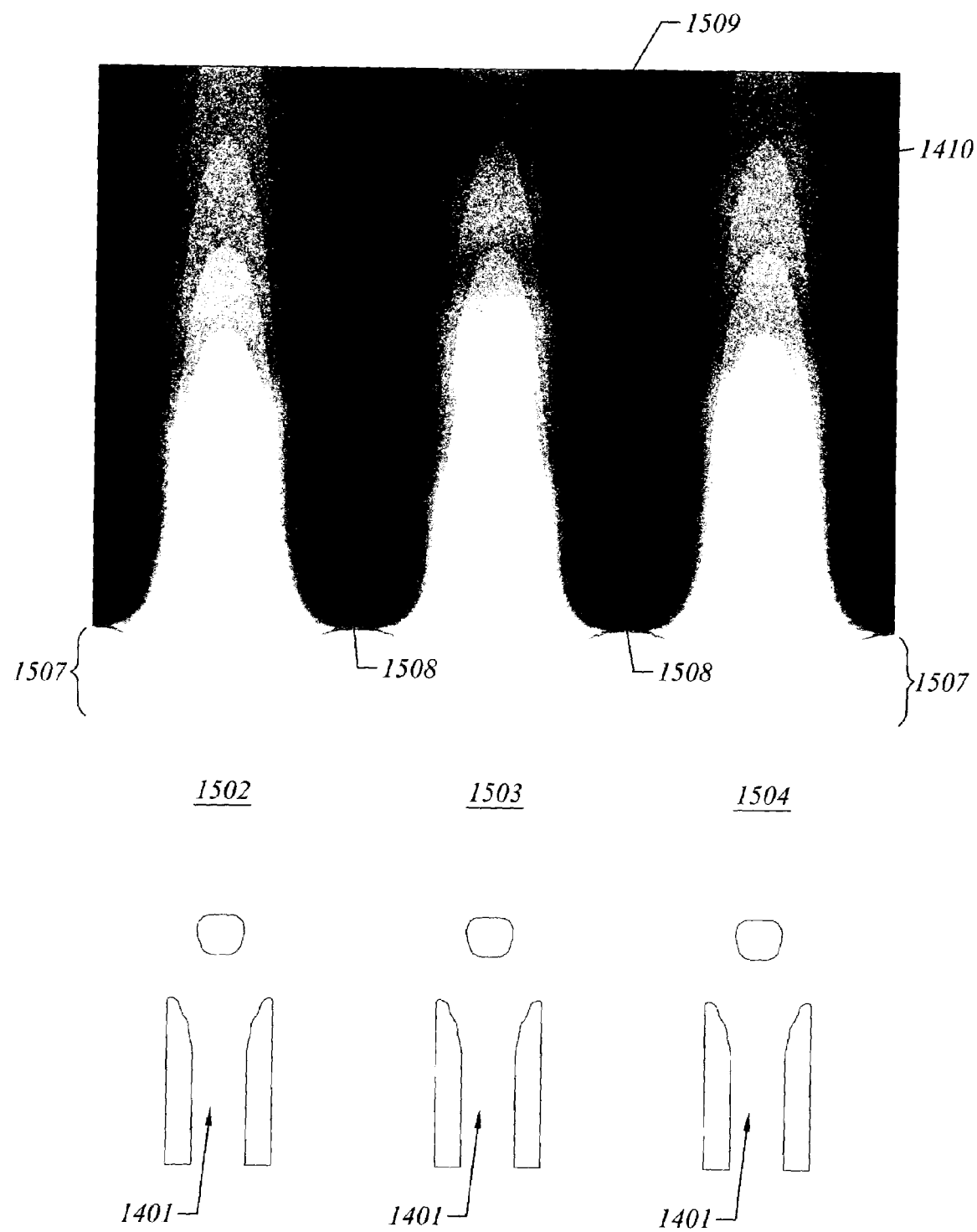
FIG. 15 illustrates a computer simulation of a sample component eluting from a channel in a microfluidic chip into a detection cell according to another embodiment of the present teachings.

FIG. 15 illustrates a computer simulation of a sample component eluting from a channel in a microfluidic chip into a detection cell according to another embodiment of the present teachings. Specifically, FIG. 15 is similar in all respects to FIG. 14 except that the electrode 1507 (shown only as a space that traverses the width of the detection cell 1404) has an applied voltage of –1V (i.e., –1 volts less than the potential at that point in the system). Specifically, the type of electrode simulated in this Example is a mesh-type electrode. In comparison to FIG. 14, the eluted sample components 1502, 1503, 1054 from each of the respective channels 1401 remain well separated as they traverse through the detection cell 1404, as shown by the dark areas 1508 which extend along the length of the detection cell to its outlet end 1509 indicating the confinement of each of the eluted sample components to its respective sample flow path.

As shown, there is no significant overlap of the eluted sample components even a significant distance from the electrode 1507. This information may be used to determine the placement of the light source used to detect the eluted sample components in the detection cell. For example, the light source or laser may be placed a relatively significant distance downstream of the electrode to minimize any interference from the electrode on the light being sent through the detection cell.

EXAMPLE 9

Figure 16:
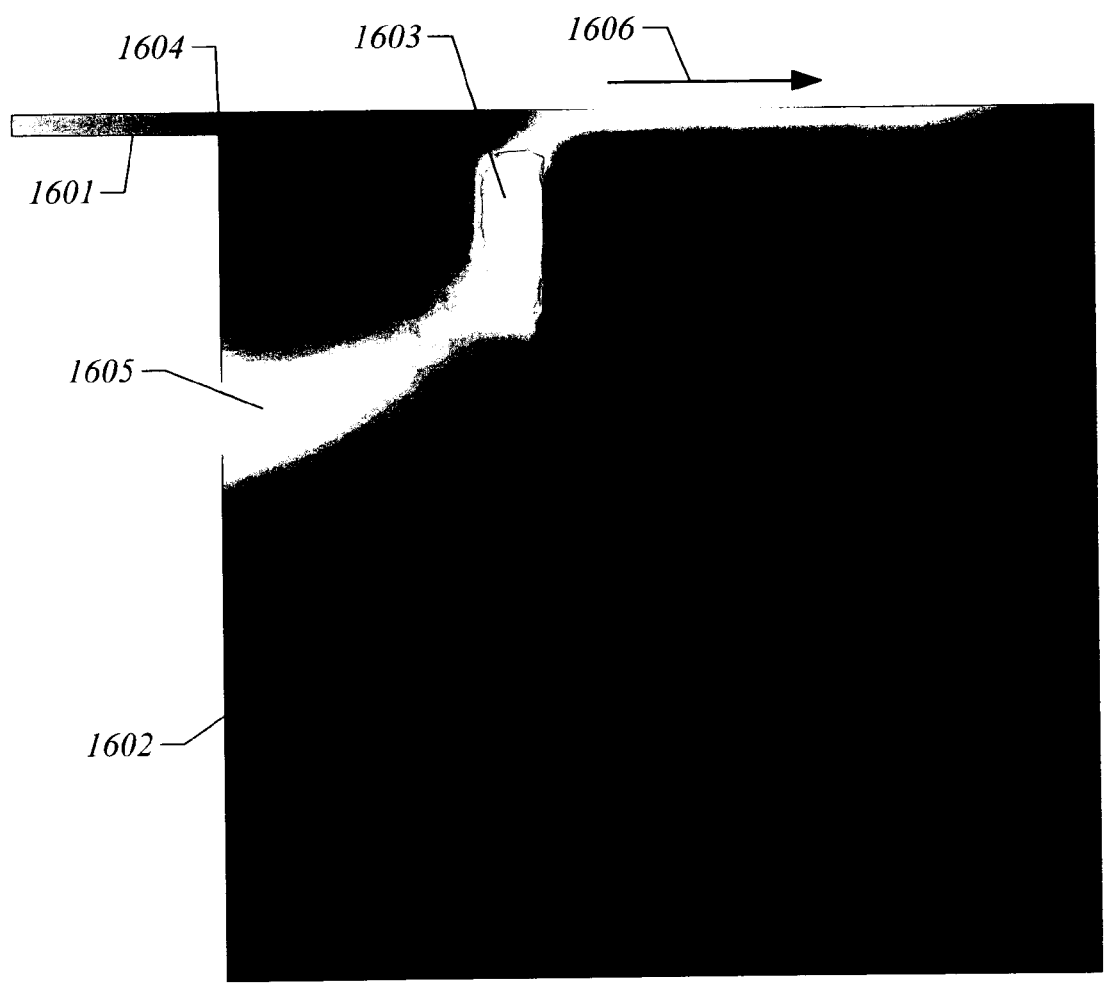
FIG. 16 illustrates a computer simulation of a sample component eluting from a channel in a microfluidic chip into a detection cell according to another embodiment of the present teachings.

FIG. 16 illustrates a computer simulation of a sample component eluting from a channel in a microfluidic chip into a detection cell according to another embodiment of the present teachings. Specifically, FIG. 16 is a side view of a channel 1601 that empties into a detection cell 1602. Also shown is an electrode 1603 positioned away from the outlet 1604 of the channel 1601. The eluted sample component 1605 has traversed from the channel outlet 1604 in a fan-shaped manner. The eluted sample component 1605 is also passing through the electrode 1603 and further along the detection cell downstream of the electrode in the direction indicated by arrow 1606. The eluted sample component 1605 in this case is not a discrete band of sample but is a continuous eluted sample component, whose concentration is higher in the lighter shaded areas. Therefore, it can be observed that the electrode 1603 is confining the eluted sample since the fan-shaped distortion evident upstream of the electrode 1603 has been curtailed.

It should be appreciated that this Example shows the highest concentration of the eluted sample component at the electrode 1603. This indicates that the eluted sample component is actually concentrating or remaining near the electrode 1603 while a remainder of the eluted sample component is passing through the electrode 1603 and along the detection cell. It is believed that once the charged DNA eluted sample touches the electrode 1603 that portion of the eluted sample component is no longer under the influence of any electrical field and basically becomes stationary. As a result, this illustrates that one embodiment would be to locate the electrode 1603 immediately adjacent to the outlet 1604 of the channel 1601 so that there is no electrical field created between the outlet 1604 and the electrode and the eluted sample component can only -move forward into and through the detection cell.

The foregoing descriptions of specific embodiments of the present teachings are presented for purposes of illustration and description. They are not intended to be exhaustive or to limit the present teachings to the precise forms disclosed, obviously many modifications and variations are possible in view of the above teachings. The embodiments were chosen and described in order to best explain the principles of the present teachings and their practical applications, to thereby enable others skilled in the art to best utilize the present teachings and various embodiments with modifications as are suited to the particular use contemplated. Furthermore, the order of steps in the method are not necessarily intended to occur in the sequence laid out. It is intended that the scope of the present teachings be defined by the following claims and their equivalents.

All references cited herein are incorporated herein in their entirety by reference and for all purposes to the same extent as if each individual publication or patent or patent application was specifically and individually indicated to be incorporated by reference in its entirety for all purposes.

What is claimed is:

1. A microfluidic apparatus. comprising:
a body defining at least one channel that extends through said body, said channel including an inlet and an outlet; and
an electrode positioned in proximity to said body, wherein said electrode defines a plurality of openings corresponding to said outlet of said at least one channel through which an eluted sample component may pass.
wherein said body further defines a plurality of channels extending through said body, each having a respective outlet from which a corresponding plurality of eluted sample components may pass; wherein said body defines a notch between each of said outlets; and
wherein said electrode conforms to at least a portion of a surface of said notch.

2. The microfluidic apparatus of claim 1, wherein said electrode comprises a coating on a surface portion of said notch.

3. The microfluidic apparatus of claim 2, wherein said coating comprises palladium.

4. The microfluidic apparatus of claim 2, wherein said electrode comprises a bubble-free electrode.

5. An electrophoresis system, comprising:
a microfluidic chip defining a plurality of channels passing therethrough, each of said channels having an inlet and an outlet;
a first electrode in electrical communication with said inlet of each of said channels;
a second electrode in electrical communication with said outlet of each of said channels; and
a third electrode in electrical communication with said outlet of each of said channels, wherein said third electrode is positioned to provide an electrical field to at least partially confine an eluted sample component passing from any of said channels,
wherein said microfluidic chip further defines a notched portion at an outlet end of said microfluidic chip between each of said outlets, such that the electrical field extends along a portion of the length of each of said channels, and
wherein said third electrode is attached to said outlet end of said microfluidic chip and conforms to said notched portion.

6. The system of claim 5, wherein said third electrode comprises a bubble-free electrode.

7. The system of claim 5, wherein said third electrode comprises a coating on said notched portion.

8. The system of claim 7, wherein said coating comprises palladium.

* * * * *